United States Patent [19]

Ackerman et al.

[11] Patent Number: 4,665,621
[45] Date of Patent: May 19, 1987

[54] MEASURING PROBE

[75] Inventors: Jerome B. Ackerman, 155 W. 13 St., New York, N.Y. 10011; Thomas T. Ackerman, Fairfield, Conn.; Mitchell N. Ackerman, Providence, R.I.; Herbert J. Hedberg, N. Attleboro, Mass.

[73] Assignee: Jerome B. Ackerman, New York, N.Y.

[21] Appl. No.: 846,180

[22] Filed: Mar. 31, 1986

[51] Int. Cl.$^4$ ............................ A61B 5/05; G01B 7/26
[52] U.S. Cl. ..................................... 33/513; 33/169 B; 433/32
[58] Field of Search ................. 33/513, 169 B, 169 R; 433/32

[56] References Cited

U.S. PATENT DOCUMENTS

| | | | |
|---|---|---|---|
| 3,916,529 | 11/1975 | Mousseau | 33/169 B |
| 3,943,914 | 3/1976 | Grenfell et al. | 433/32 |
| 3,979,835 | 9/1976 | Sumption et al. | 33/169 B |
| 4,164,214 | 8/1979 | Stark et al. | 433/32 |

OTHER PUBLICATIONS

"The Accuracy of Clinical Parameters in Detecting Periodontal Disease Activity", Ryan, Robert J.; JADA vol. III, Nov., 1985, pp. 753–760.
"Fiber Optic Links"–7 pages–Molex.
"An Electronic 'Hammer' Beats Out X Rays"–Gosch, John–Electronics, Mar. 3, 1986, p. 25.
"The Periogram System"–William L. O'Neill–3 pages.

Primary Examiner—Willis Little
Attorney, Agent, or Firm—Blum, Kaplan

[57] ABSTRACT

An apparatus for measuring the distance between two points in a patient undergoing dental diagnosis or treatment which includes a housing having an end which is placeable adjacent a first of said points. A distance measurement apparatus is coupled to the housing and provides an output signal representative of the distance between the two points. An analyzer responsive to the output signal determines the distance. The distance measurement apparatus may include an elongate probe slidably mounted in the housing so as to be extendable from one point to the other when the end of the housing is placed adjacent one said point. A probe actuator causes the probe to slide in the housing. A motion detector is responsive to motion of the probe with respect to the housing and provides an output which is useful for determining the position of the probe with respect to the housing. The probe actuator may be manually activated. A friction mechanism may be provided to assure that a predetermined force is utilized to move the probe so that measurement accuracy is enhanced. The analyzer may include a microcomputer for analyzing the data produced and for presenting the data in a displayable format.

54 Claims, 23 Drawing Figures

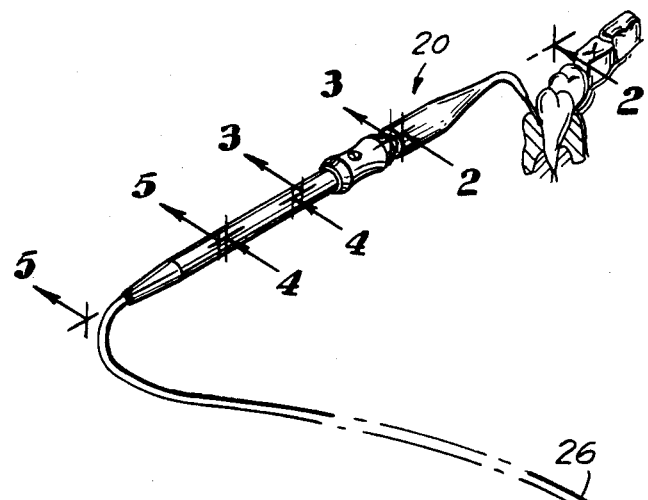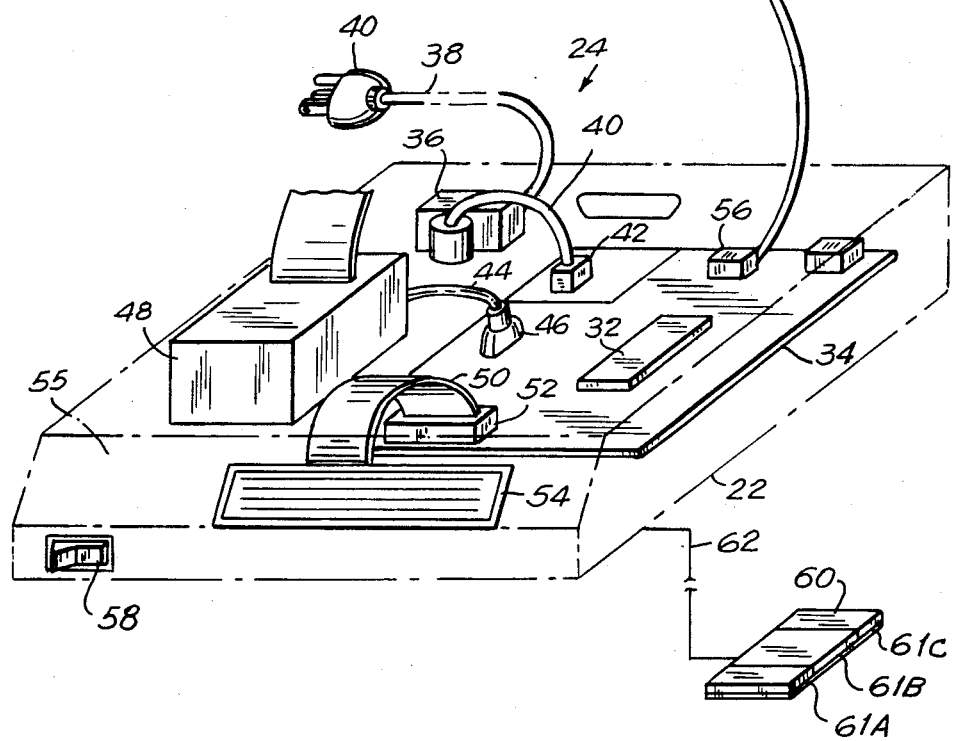
FIG. 1

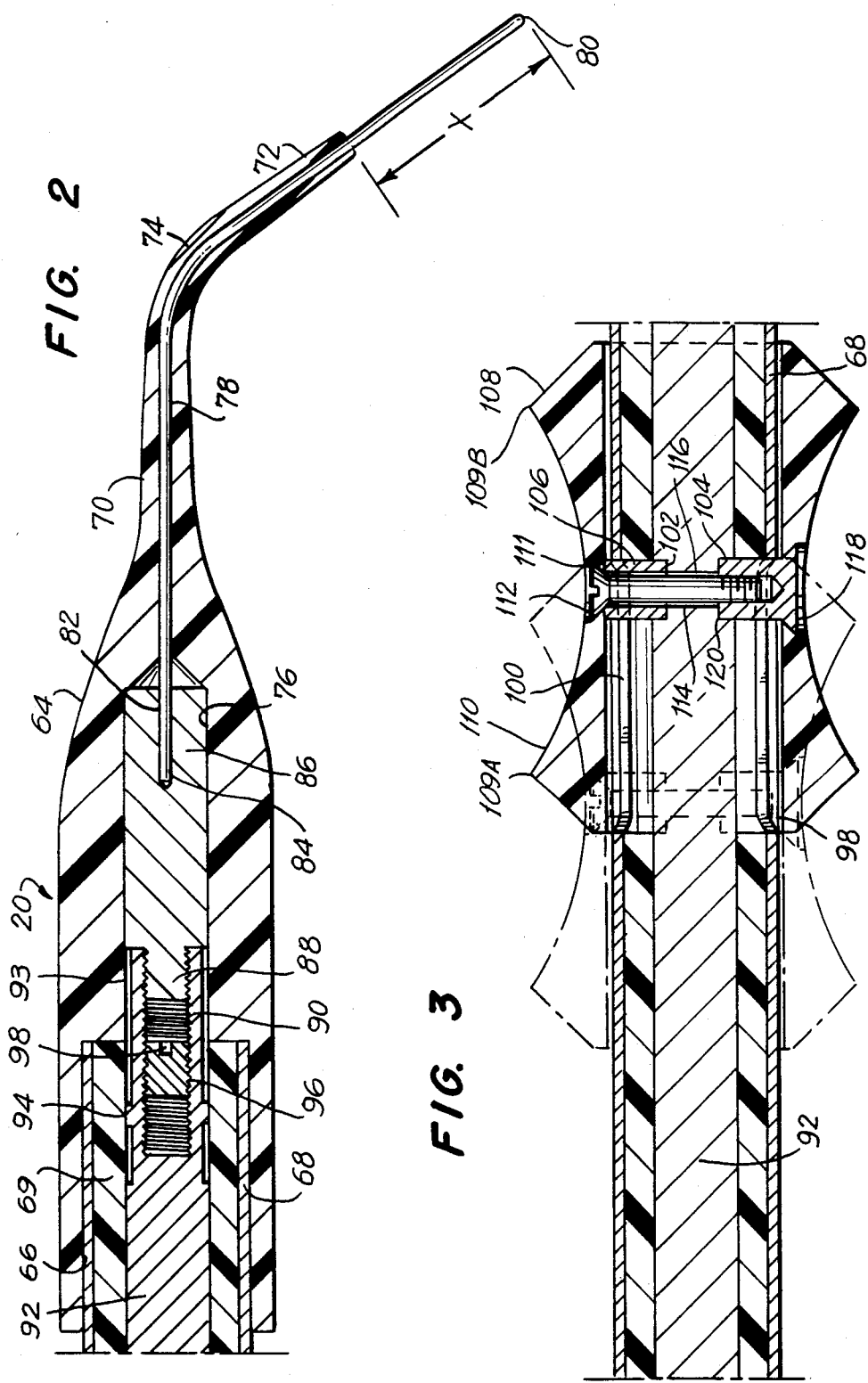

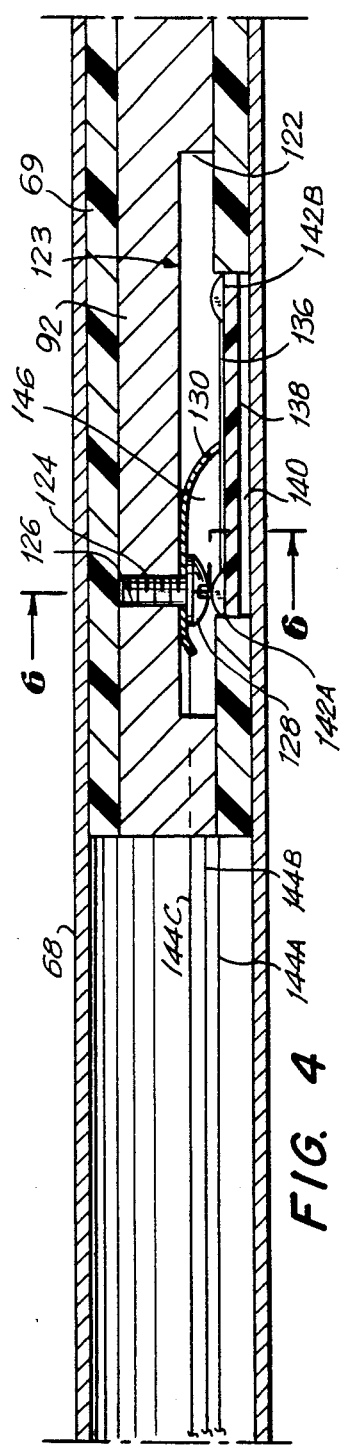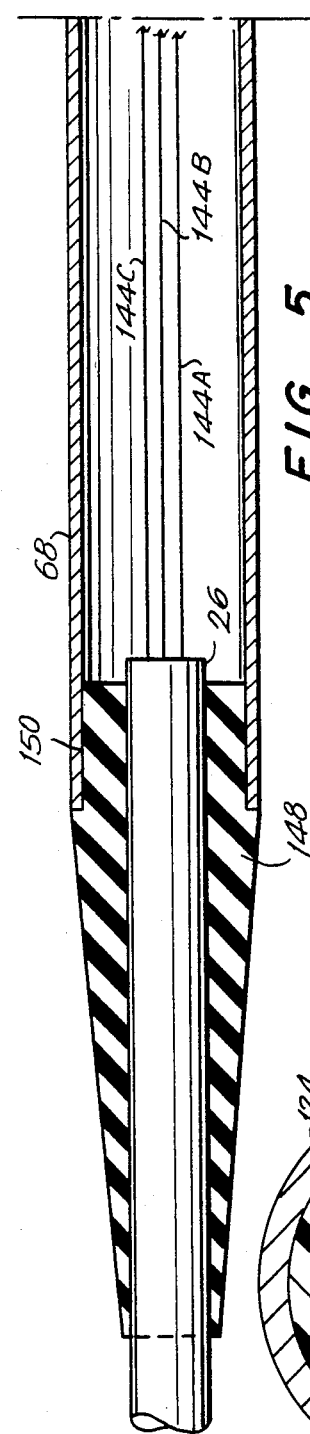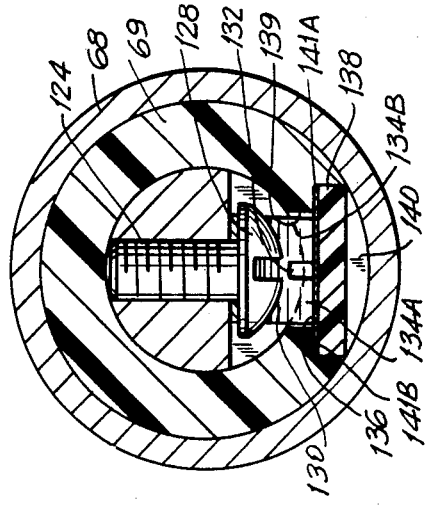

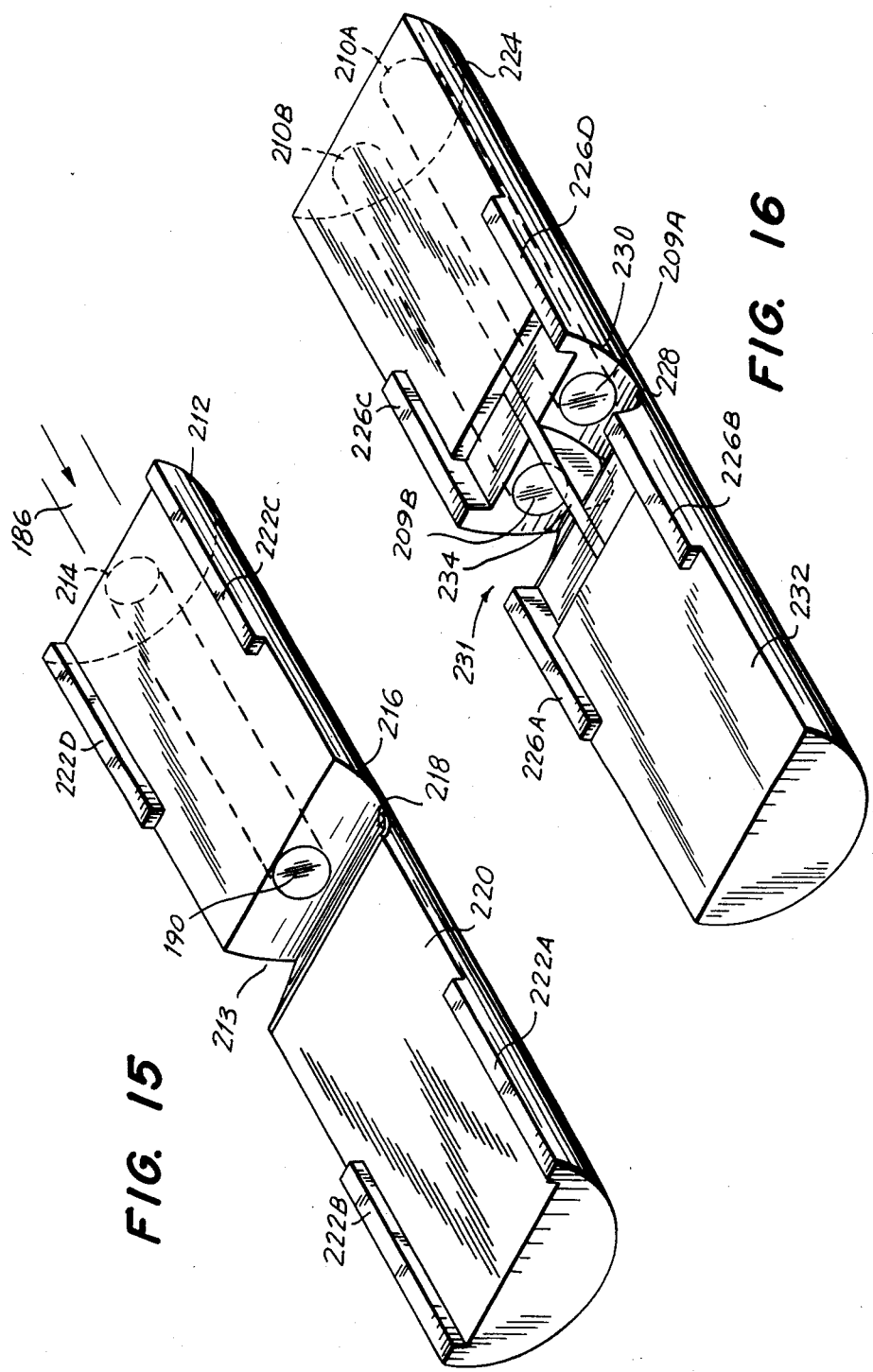

TABLE 1

ENCODER STRIP
MOVING TO RIGHT

CHANNEL

| A | B |
|---|---|
| 0 | 0 |
| 0 | 1 |
| 1 | 1 |
| 1 | 0 |
| 0 | 0 |
| 0 | 1 |
| 1 | 1 |
| 1 | 0 |
| 0 | 0 |

TABLE 2

ENCODER STRIP
MOVING TO LEFT

CHANNEL

| A | B |
|---|---|
| 0 | 0 |
| 1 | 0 |
| 1 | 1 |
| 0 | 1 |
| 0 | 0 |
| 1 | 0 |
| 1 | 1 |
| 0 | 1 |
| 0 | 0 |

*FIG. 18A*

TABLE 3

| | | |
|---|---|---|
| 0 | 1 | OFFSET = 00 (=0) |
| 1 | 1 | OFFSET = 01 (=1) |
| 0 | 0 | OFFSET = 10 (=2) |
| 1 | 0 | OFFSET = 11 (=3) |

*FIG. 18B*

MEASURING PROBE

BACKGROUND OF THE INVENTION

The present invention is generally directed to a probe and measuring apparatus for use in dentistry and medicine in particular for use in the accurate evaluation of periodontal pocket depth or during procedures that require the accurate evaluation of the depth of penetration and length of root canal.

Several parameters useful in detecting periodontal disease activity have been addressed by Ryan, R. J. in The Accuracy of Clinical Parameters in Detecting Periodontal Disease Activity, JADA, 111: 753–760, 1985. These parameters are plaque assessment, gingival assessment, gingival crevicular fluid, radiographic assessment and periodontal probing assessment. Another parameter is malocclusion. With the exception of periodontal probing assessment these parameters are often poor indicators of the current state of activity of periodontal disease. For example, it has been noted that quantitative plaque assessment is of little value except as a motivational tool. Qualitative plaque assessment, including culturing techniques, is somewhat more accurate in identifying sites that will undergo periodontal deterioration. However, sophisticated equipment and technique is required and this approach may not be feasible or practical in a typical clinical setting.

Inflammation of the gums is often a poor indicator of ongoing periodontal disease activity. Often disease is present with minimal evidence of inflammation. The chief benefit of gingival assessment seems to be in detecting the presence of enlargement of the tissues and the potential for associated pocketing.

The evaluation of gingival crevicular fluid serves to highlight a shift from a healthy to an inflamed gingival state. However, experience has indicated that this is not necessarily indicative of impending or active periodontal disease.

Radiographic assessment has several shortcomings. The relationship between soft and hard tissue is not easily and consistently shown. Further, radiographic assessment tends to shown less bone loss than has actually occurred. In addition, significant bone loss must take place before it can be detected. Finally, radiographic assessment is generally only useful for retrospective analysis, and is not regarded as a good indicator of existing periodontal disease activity.

One of the most useful diagnostic tools for determining the presence and severity of periodontal disease is the periodontal probe. Pocket depth is a particularly useful indicator of the extent of periodontal destruction. Potentially, small changes in the attachment level and in pocket depth can be detected with a high degree of accuracy. However, the amount of force used and the diameter and shape of the probe effect the measurement. Further, different examiners may perform measurements in slightly different ways. Finally, when conventional charting forms and techniques are used, recording periodontal probe measurement data is time consuming and, if done without an assistant, requires interruption in the examination and reinsertion of the probe to record the measurements. Further, evaluations of the progress of disease are difficult to make unless made on a chart which permits comparisons of current and previous measurements.

In another area, when root canal treatment is being performed, it is possible to use conductive type measuring devices to determine when the apex of the root has been reached. However, when the root canal is being packed or filled, it is generally not possible to ascertain whether such packing has taken place as far as the apex of the root canal without X-rays. While radiographic techniques can be used, it is undesirable for the patient to be repeatedly exposed to X-rays to determine whether adequate packing has taken place.

Accordingly, there is a need for a dental instrument which probes gingival pockets or a root canal to allow precise and accurate determination of depth of penetration of the probe. There is also a need for a device which permits measurements to be taken without variations due to the examination technique of the individual practitioner. Further, there is a need for an instrument which records, displays and charts data concerning depth of penetration in a manner useful to the dentist.

SUMMARY OF THE INVENTION

The invention is generally directed to an apparatus for measuring the distance between two points in a patient undergoing medical or dental diagnosis or treatment which includes a housing having an end which is placeable adjacent to a first of said points. A distance measurement means is coupled to the housing and provides an output signal representative of the distance between the two points. An analyzing means responsive to the output signal reports the distance measured. The distance measurement means may include an elongate probe slidably mounted in the housing so as to be extendable from one point to the other when the end of the housing is placed adjacent to one said point. A probe actuating means causes the probe to slide in the housing. A motion detection means is responsive to motion of the probe with respect to the housing and provides an output which is useful for determining the position of the probe with respect to the housing.

The probe actuating means may be manually activated. Further, means may be provided to assure that a relatively constant force is provided to move the probe so that measurement accuracy is enhanced.

The analyzing means may include a microcomputer for analyzing the data produced and for presenting said data in a displayable format.

Accordingly, it is an object of the instant invention to provide an apparatus for precisely and accurately measuring the distance between two points in the patient.

Another object of the invention is to provide an apparatus for conveniently recording and displaying the data obtained.

A further object of the invention is to provide an apparatus which permits accurate measurement of the depth of periodontal pockets with minimum discomfort or risk to the patient.

Still another object of the invention is to provide an apparatus wherein the impact of variables associated with the examination technique are eliminated.

Yet another object of the invention is to provide an apparatus which permits measurements of the depth of penetration of an excavation in a root canal.

Still other objects and advantages of the invention will in part be obvious and will in part be apparent from the specification.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the invention, reference is had to the following description taken in connection with the accompanying drawings, in which:

FIG. 1 is a perspective view of an apparatus according to the invention;

FIG. 2 is a cross-sectional view taken along line 2—2 of FIG. 1;

FIG. 3 is a cross-sectional view taken along line 3—3 of FIG. 1;

FIG. 4 is a cross-sectional view taken along line 4—4 of FIG. 1;

FIG. 5 is a cross-sectional view taken along line 5—5 of FIG. 1;

FIG. 6 is a cross-sectional view taken along line 6—6 of FIG. 4;

FIG. 15 is a perspective view of a housing portion for use with the encoder embodiment of FIG. 14;

FIG. 16 is a perspective view of a housing portion which mates with the housing portion illustrated in FIG. 15;

FIG. 18A is a chart showing the data produced by the encoder of FIGS. 14 to 16;

FIG. 18B is a table used in computing direction and extent of motion in response to the data of FIG. 17.

DETAILED DESCRIPTION OF THE PREFERRED EMBODIMENTS

Figure 7:
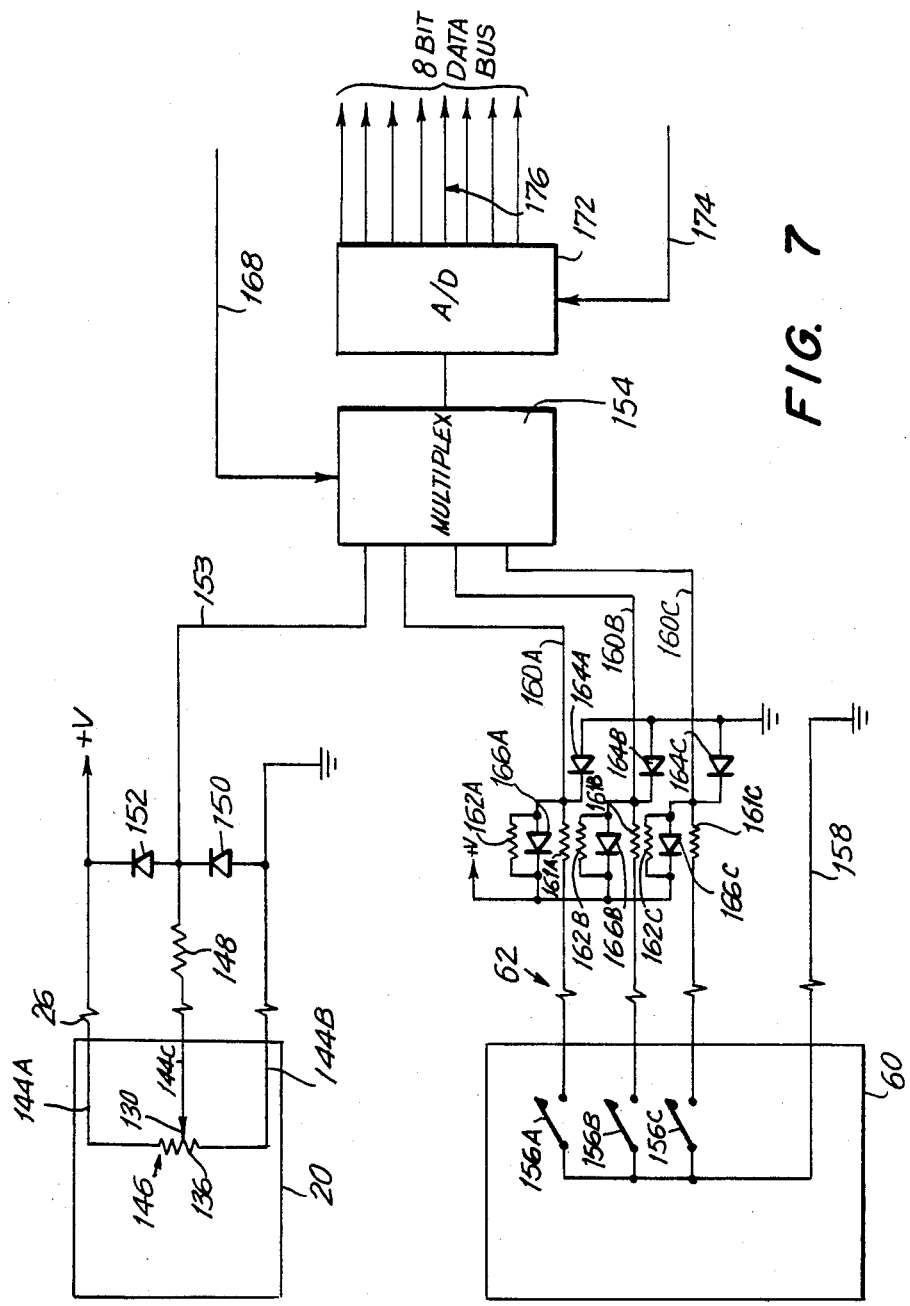
FIG. 7 is a schematic diagram showing the interconnection of various components illustrated in FIG. 1.

The present invention is directed to an apparatus for measuring distances between points in a patient undergoing medical or dental diagnosis or treatment.

In the field of dentistry the present invention may be used to assist in the diagnosis of periodontal disease, to determine the depth of penetration into a root canal, as a general measuring instrument to determine the extent to which the gums have receded to assist in making measurements of interest in orthodontia or to evaluate the extent of a gap between the teeth such as that resulting from occlusion.

Reference is made to FIG. 1, wherein a dental probe 20 is connected to a housing 22 of a data processing and display unit 24 by means of a cable 26. Probe 20 is used to measure distances between points in the mouth such as the length of the clinical crown of a tooth 28, the depth of a pocket between the tooth 28 and the adjacent gum 30 or the depth of a root canal excavation (not shown) in tooth 28.

Data from probe 20, carried to unit 24 by cable 26, is processed by a microcomputer 32 on circuit board 34. Microprocessor 32 may advantageously be a single chip device such as one of the Mitsubishi 740 series having a built in RAM, ROM, EPROM and A/D converter, the actual configuration being selected in accordance with the program requirements.

Circuit board 34 receives power from a power supply including a transformer 36 which is connected by a standard power cord 38 to a standard plug 40 which fits into a conventional power outlet of a type commonly found in homes and offices. Power from the power supply is conducted to circuit board 34 by means of a cable 40. A connector 42 at the end of cable 40, releasably mates with a corresponding connector (not shown) on circuit board 34.

Another cable 44, having a connector 46, serves to releasably electrically connect a compact printer 48 to circuit board 34. Yet another cable 50 having a connector 52 for attachment to circuit board 34 serves to releasably electrically connect a display 54, mounted to front panel 55 to circuit board 34. A connector 56 serves to releasably connect cable 26 to circuit board 34. A foot pedal switch 60 is connected to unit 24 and ultimately to circuit board 34 by a cable 62. Foot pedal switch 60 has three foot pedals 61A, 61B and 61C which are independently movable so as to supply signals, via cable 62, ultimately to microcomputer 32 to choose one of several modes of operation of microcomputer 32 in analyzing and organizing the data obtained from probe 20 as more fully described below. An extension (not shown) of cable 62 has a connector (not shown) which serves to releasably electrically connect cable 62 to circuit board 34.

Thus, all electrical connections to circuit board 34 are made by means of releasable connectors so that circuit board 34 is easily removed for servicing. A switch 58 connected to transformer 36 of the power supply, in a manner well known in the art, serves as an on/off power switch for unit 24.

Referring to FIG. 2, probe 20 has a nylon tip 64 having a cylindrical opening 66 at an end thereof which is configured to receive a probe housing 68. Opening 66 and the external diameter of probe housing 68 are sized so that probe tip 64 surrounds housing 68 with an interference fit with just enough force therebetween to hold probe tip 64 in place; thus probe tip 64 can be removed by application of a reasonable amount of force without damage to any of the components of probe 20 or to probe tip 64. An internal sleeve 69, formed of plastic, is provided within housing 68. Alternatively, a twist locking mechanism (not shown) may be used to removably secure probe tip 64 to probe housing 68.

Probe tip 64 has a conically tapered portion 70 which bends to an end 72 which is of smaller diameter than portion 70. Probe tip 64 also has a elongate axial passageway 74 extending from end 72 and through portion 70 to a larger diameter opening 76 which extends to opening 66.

A probe member 78, which is preferably a nylon monofilament having a diameter of approximately 0.024 inch (0.61 mm) is closely received in passageway 74 so that it can slide therein. Probe member 78 may be formed with a suitable additional material so that it is radio-opaque; that is, so that it is capable of absorbing X-rays to the extent that its presence in a root canal or a gingival pocket will be readily displayed on an X-ray of the area being probed. Thus, end 80 of probe 78 may be urged to protrude from probe tip 64 as more fully described below.

End 82 of probe member 78 is received in an axially extending opening 84 of a chuck member 86. The relative diameters of opening 84 and probe member 78 are selected so that an interference fit exists therebetween and so that probe member 78 may be removed from chuck member 86 upon the application of a reasonable force which is insufficient to cause damage or rupturing of probe member 78 or of chuck member 86, and components associated therewith. Alternatively, any one of a number of well known locking mechanisms (not shown) may be used.

Chuck member 86 has a threaded cylindrical portion 88 which extends into a cylindrical opening 90 of an actuating member 92. Cylindrical opening 90 has an internal thread which corresponds to and mates with the external thread of member 88.

Actuating member 92 has an outer circumferential wall 93 which defines a section having a diameter less than the internal diameter of internal sleeve 69. An annular shoulder 94, to the rear of the reduced section, extends around the circumference of actuating member 92 so as to frictionally engage the internal surface of internal sleeve 69. The force of engagement is determined by the axial position of a screw 96 in central cylindrical opening 90. Screw 96 may be rotated by means of a tool, such as an Allen wrench (not shown), extending into an axial opening 98 in the end of screw 96. Access to opening 98 is provided by unscrewing chuck member 86 from actuating member 92. While annular shoulder 94 is sized and shaped so as to contact the internal surface of internal sleeve 69, screw 96 has a diameter which is sized so that, when it is rotated so as to approach the plane of annular shoulder 94, it forces annular shoulder 94 against the internal surface of internal sleeve 69 with increasing force. Thus, the force needed to overcome friction between annular member 94 and the internal surface of internal sleeve 69 may be set by rotary adjustment of the position of screw 96.

In order to facilitate disconnection of chuck member 86 from actuating member 92, the larger forward portion of chuck member 86, which receives probe member 78 has a non-circular cross section so that rotation of probe tip 64 with respect to housing member 68 serves to rotate chuck member 86 with respect to actuating member 92. Opening 76 of probe tip 64 has a corresponding non-circular cross section to closely receive chuck member 86 while permitting chuck member 86 to slide along opening 76.

As illustrated in FIG. 3, hollow cylindrical probe housing 68 and internal sleeve 69 have two diametrically opposed slots 98 and 100 extending longitudinally thereof. Actuating member 92 has two cylindrical flat bottomed openings 102 and 104 which are located on a common axis extending radially with respect to actuating member 92. Openings 102 and 104 respectively receive bushings 106 and 118. A control sleeve 108 has an inner diameter large enough to permit it to slide along housing 68 and an outside surface with spaced apart annular peaks 109A and 109B which define the ends of a concave peripheral surface 110. Surface 110 has an opening 111 for receiving the head 112 of a screw 114 that extends through bushing 106, and a radial passageway 116 in actuating member 92 which serves to connect opening 102 and opening 104. The end of screw 114 opposite head 112 is received in bushing 118 which has an opening 120 having an internal thread which mates with the external thread of screw 114. The outer diameters of bushings 106 and 118 are selected, respectively, so that bushings 106 and 118 can slide from one end to the other end in slots 98 and 100. Thus, manually moving sleeve 108 with respect to probe housing 68 causes actuating member 92 to slide within probe housing 68 and causes probe member 78 to slide within probe tip 64. The position of slots 98 and 100 along probe housing 68 and the position of opening 114 with respect to actuating member 92 are chosen so that when sleeve 108 is moved to the right in FIG. 3 (so that bushings 106 and 118 are at the right ends of slots 100 and 98 respectively) maximum extension of probe member 78 from probe tip 64 to the dimension indicated as X in FIG. 2 will occur. Typically, this dimension should be in the order of approximately 0.60 inches (1.5 cm) for most dental applications.

Referring to FIG. 4, a slot 122 which defines a planar surface 123 is provided in the end of actuating member 92, removed from the end coupled to chuck member 86. A screw 124 is received in a hole 126 extending in the radial direction with respect to probe housing 68. The head 128 of screw 124 serves to secure a resilient, conductive metallic member 130 to actuating member 92. One end of member 130 has a slot 132 which serves to bifurcate that end into two portions 134A and 134B which contact a resistive element 136 formed on an insulating member 138. Insulating member 138 fits within probe housing 68 so that it is parallel to a line which is tangent to the internal surface thereof and parallel to the longitudinal axis of probe housing 68 so as to define a space 140 between insulating member 138 and probe housing 68. Internal sleeve 69 has an opening 139 for receiving metallic member 130 and shoulders 141A and 141B for receiving insulating member 138 (FIG. 6). Each end of resistive layer 136 has formed thereon an electrical contact 142A and 142B, respectively.

Contacts 142A and 142B are connected (not shown) to conductors 144A and 144B which extend from cable 26 (FIG. 5) through a passageway in internal sleeve 69. Cable 26 is received in a strain relief member 148 having a tapered conical shape and slightly reduced diameter portion 150 which is securely held in the end of probe housing 68.

A conductor 144C, also extending from cable 26 through a passageway in the end of actuating member 92 (not shown), is connected to screw 124 so that its end is in electrical contact with metallic member 130. Conductor 144C has sufficient excess length so that no significant tension is produced therein when actuating member 92 moves to fully extend probe member 78 from housing tip 64 by moving to its extreme right hand position as noted above.

Thus, metallic member 130 and resistive element 136, when excited by a voltage applied to conductors 144A and 144B form a potentiometer 146, with the potential of conductor 144C varying with the position of the ends 134A and 134B of metallic member 130 along the length of resistive element 136. As actuating member 92 is moved to extend probe member 78 from probe tip 64, the voltage on conductor 144C will vary.

FIG. 7 illustrates the electrical connection of probe 20 and pedal 60 to components on circuit board 34. An excitation voltage is supplied to one end of potentiometer 146 in probe 20 by means conductor 144A connected to a low positive voltage $+V$, such as 5 volts, which is generated by the power supply in housing 22 and is also used to drive microcomputer 34, printer 48 and display 54. Conductor 144B connects the other end of potentiometer 146 to ground. Conductor 144C, connected to metallic member 130 which serves as a slider for potentiometer 146, is connected to one end of a resistor 148. The other end of resistor 148 is connected to the junction of a first diode 150 and a second diode 152. This junction is also connected by means of a conductor 153 to one analog input of analog multiplexer 154. Diodes 150 and 152 are normally reverse biased, but serve as protection elements against the buildup of excess potentials, such as static charges or induced voltages which would damage multiplexer 154.

Each foot pedal 61A, 61B and 61C of foot pedal switch 60 is connected to a respective switch 156A, 156B and 156C. One end of each switch is grounded by a conductor 158 extending along cable 62. The ungrounded ends of each of switches 156A, 156B and 156C are connected by conductors 160A, 160B and 160C respectively, extending along cable 62, to respective series resistors 161A, 161B and 161C which are in turn connected to respective inputs of multiplexer 154. Each conductor 160A, 160B and 160C is connected through a respective pull-up resistor 162A, 162B and 162C to the positive supply voltage, $+V$. Further, respective diodes 164A, 164B and 164C extend from conductors 160A, 160B and 160C to ground. Respective diodes 166A, 166B and 166C are connected in parallel with pull-up resistors 162A, 162B and 162C and thus extend from conductors 160A, 160B and 160C respectively to the positive supply voltage, $+V$. Thus, diodes 164A, 164B, 164C, 166A, 166B, and 166C, which are all reverse biased, and the resistors associated therewith, form three protection networks for the three respective inputs of multiplexer 154 to which conductors 160A, 160B and 160C are electrically connected through resistors 161A, 161B and 161C respectively.

A control line 168 is connected to a channel selection input of multiplexer 154. A signal supplied from microcomputer 32 to control line 168 determines which of the four inputs to multiplexer 154 is connected to the output 170 of multiplexer 154 at any given time. This function of mode selection is under the control of the software or program associated with microcomputer 32, as more fully described below.

The output of multiplexer 154 is connected to the input of analog to digital converter 172 by a conductor 170. A control line 174, which also receives a signal from microcomputer 32 at appropriate times causes analog to digital converter 172 to commence the conversion of the analog voltage present on conductor 170 to digital form. The digital output is supplied to microcomputer 32 by multiple digital data lines 176. Thus, the output of analog to digital converter 172 is one of a digital number representing the analog voltage generated by potentiometer 146 of probe 20 between zero volts and $+V$ volts, zero volts, or $+V$ volts, depending upon whether the input of multiplexer 154 that is selected by line 168 is connected to whichever one of switch 156A, 156B or 156C is open or closed. An open switch produces a digital output corresponding to $+V$ volts, while a closed switch produces a digital output corresponding to zero volts.

A major area of applicability of the invention is the measurement of the depth of gingival pockets and the recording of the pocket depth together with the location of the tooth with which the pocket is associated. When the system is turned on, as more fully described below, the program associated with microcomputer 32 initializes the system by clearing display 54 and displaying tooth number designation "01 labial". An initial depth reading of 00.0 mm is also displayed. The program then causes the printer to provide a print header block containing an identification of the instrument and a form blank to be manually filled out by the dentist by hand prior to commencing the examination. The form has fields for "Date", "Time", "Patient" and "Examined By". After the header form is printed, the software requires a command from foot pedal switch 60.

In a typical sequence of operation, sleeve 108 of probe 20 is placed at an appropriate position for calibration of zero reference and a measurement is then made. At least three methods are available for making measurements. Using the first method, probe member 78 may be withdrawn into probe tip 64 by moving sleeve 108 to the maximum extent possible toward cable 26. At this time, foot pedal 61A is pressed, closing switch 156A. This establishes a zero reference from which measurements may be taken. The pocket depth associated with the first tooth is then measured by placing the end 72 of probe tip 64 on the labial side of the first tooth at the intersection of the gum with the clincial crown, that is the exposed lateral surface of the tooth. Sleeve 108 is then moved forward toward probe tip 64, extending probe member 78 from probe tip 64 until the end 80 of probe member 78 reaches the bottom of the pocket. The dentist quickly develops a feel for when this has occurred. The voltage output of potentiometer 146 is proportional to pocket depth and is represented as a positive number.

Using this method there is no reliance upon the friction adjusting mechanism discussed above. Screw 96 may be adjusted to provide only a minimal frictional force against motion of sleeve 108. However, the second and third methods set forth below utilize the friction adjustment mechanism.

In accordance with a second method, foot pedal 61A is first pressed to provide a zero reference with probe member 78 fully retracted into probe tip 64. Probe member 78 is then fully extended by moving sleeve 108. Probe member 78 is inserted into the pocket being measured and probe 20 is manipulated without any constraints on the motion of sleeve 108 until end 72 of probe tip 64 is at the intersection of the top of the gum and the clinical crown. A measurement of pocket depth is then taken by pressing foot pedal 61B.

In accordance with a third method, probe member 78 is fully extended from probe tip 64 by moving control sleeve 108 to the fullest extent possible toward probe tip 64. End 80 of probe member 78 is then inserted into a pocket, the depth of which is to be measured. End 72 of probe tip 64 is thus positioned some distance from the intersection of the top of the gum and the clinical crown. With no fingers on sleeve 108, probe 20 is manipulated so that end 72 of tip 64 is moved to the intersection of the gum and the clinical crown. The amount of pressure exerted by end 80 of probe member 78 on the bottom of the pocket during such manipulation is determined by the position of screw 96 as in the second method. Foot pedal 61A is pressed, closing switch 156A and providing a zero reference. Sleeve 108 is then moved so as to fully retract probe member 78 into probe tip 64. Foot pedal 61B is then pressed to make a measurement which produces a negative number.

In any event, in order to take a measurement, foot pedal 61B is pressed, thus closing switch 156B when a first measurement for a particular tooth is taken. Printer 48 prints the tooth number and the designation lingual or labial before printing the depth reading. For subsequent measurements of the same tooth, only the depth reading is printed. Multiple measurements on the same tooth may be taken while switch 156B remains pressed, as a depth measurement will be printed by printer 48 and shown on display 54 periodically. The position of end 80 of probe member 78 in the gingival pocket may be changed without withdrawing to decrease the chance of trauma.

To indicate a different location, such as the next tooth number, foot pedal 61C is pressed thus closing switch 156C. The position of sleeve 108 in probe housing 68, then determines whether the displayed tooth number is incremented or decremented. When pedal 61C is pressed and sleeve 108 is moved to the rear, i.e. toward the end of probe 20 associated with cable 26, the tooth number is incremented by one number. Display 54 then shows the tooth number as incremented by displaying the next higher integer. However, if sleeve 108 is positioned toward probe tip 64 when foot pedal 61C is pressed, the tooth number will be decremented by one. Display 54 will then indicate that the tooth number as decremented by displaying the next lower integer and the appropriate designation lingual or labial.

Whether sleeve 108 is held at a position which causes incrementing or decrementing of tooth number, each time foot pedal 61C is released and then pressed again to close switch 156C, the function of incrementing or decrementing will be repeated. On the other hand, if pedal switch 61C is continuously pressed, repeated motion of sleeve 108 toward and away from the right or left extremes of its motion, will cause incrementing or decrementing of tooth number, respectively.

In typical examination sequence, it is advantageous to first increment tooth number from 16 labial as, for example, the pocket depths on the labial side of all lower teeth are examined. Then, advantageously the program operating microcomputer 32 switches to lingual and again indicates tooth number 16. Tooth number is then decremented from 16 to 1 as the lingual side of the bottom teeth are examined. The program is configured so that after examination of gingival pockets associated with the lingual side of tooth 1, upper tooth number 32 is then displayed, starting with the labial side. Tooth number is then decremented as gingival pocket depths are measured until tooth number 17 labial is reached. This represents examination of gingival pocket depths associated with the labial sides of the upper teeth. After such examination, the program designates tooth number 17 lingual. Tooth number is then incremented until tooth number 32 lingual has been examined for gingival pocket depth. This completes examination of the lingual pocket depths associated with the upper teeth and completes the procedure. A hard copy printout of the measurements taken and the location, designated by tooth number and side (lingual/labial) is available to the dentist, the patient and any other interested parties such as dental insurers to whom information may be released to document the extent of periodontal disease.

Figure 8:
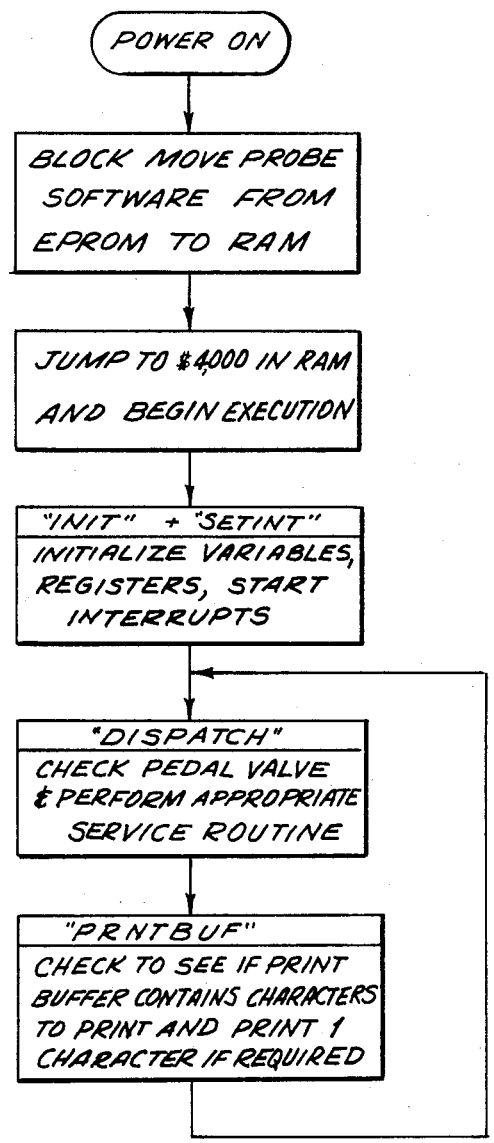
FIG. 8 is a flow diagram of the main program executed by the microcomputer of the apparatus of FIG. 1.

FIG. 8 illustrates the main flow diagram of the program executed by microcomputer 32. Operation of the software is initiated by turning on the power by means of switch 58. The program is moved from an EPROM into a RAM area of microcomputer 32 where the execution actually occurs. At the end of this block transfers of code, the program jumps to location 4000 Hex in RAM and then begins execution.

The first step of the actual program includes the execution of two subroutines INIT and SETINT. These essentially initialize all the variables, the RAM area to be used by the program, various registers in the CPU of microcomputer 32, program an interrupt generator of microcomputer 32, and start the interrupts. After this initialization phase, the program moves on to execute a subroutine called "DISPATCH". The function of this program module is to check the current value of the foot pedal; that is what the operator desires to do and to then perform the appropriate service routine. Having completed DISPATCH, the software moves on to the next subroutine, print buffer (PRNTBUF), which functions to check the contents of a printer buffer associated with microcomputer 32 for anything that needs to be printed. If something is found, that character is sent to printer 48. The program then loops around and goes back to the top of the subroutine DISPATCH. The program stays in this loop during normal operation of probe 20. In summary, in this loop, first a check is performed to determine what needs to be done, when a check of the printer buffer is performed to determine if something should be printed. This loop is referred to as the main or foreground loop, and is executed on a continuous basis. However, it can be interrupted by more important subroutines; that is by interrupt generation functions of microcomputer 32.

Figure 9:
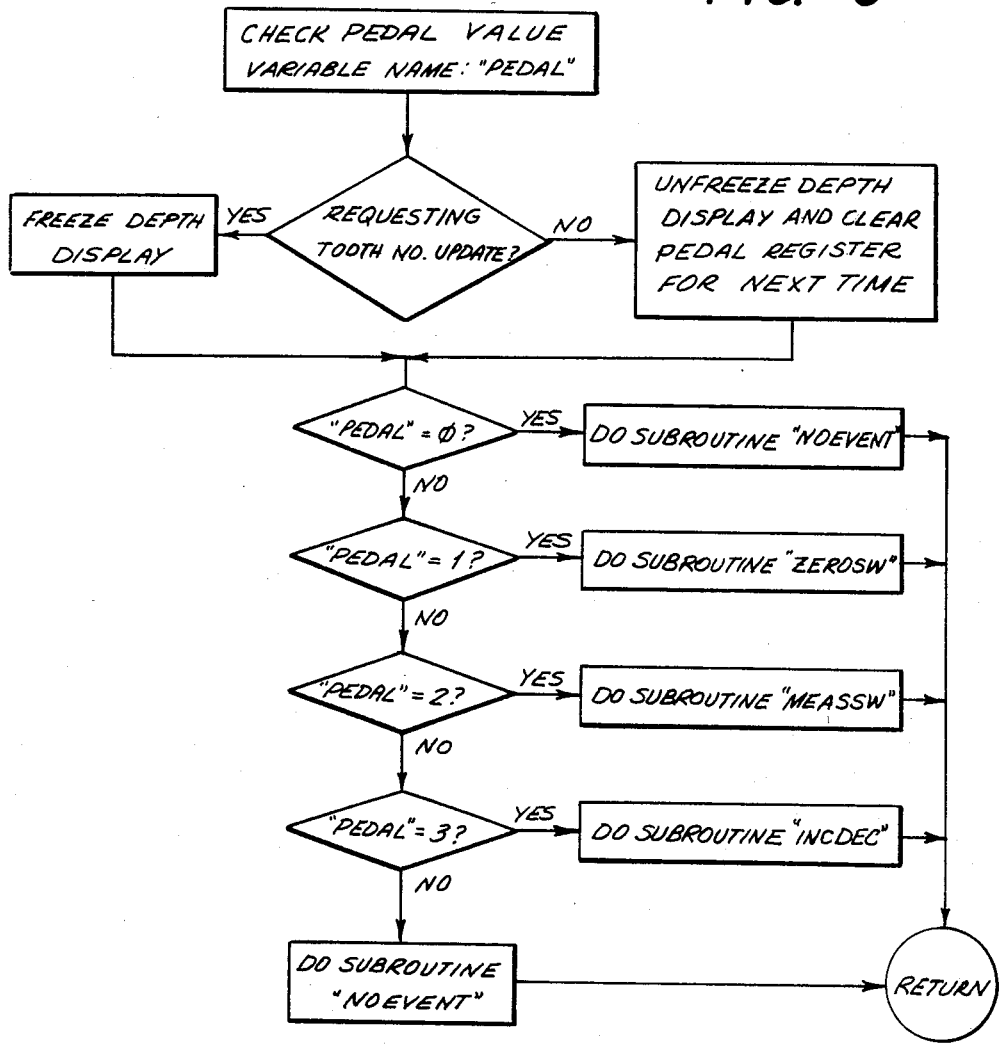
FIG. 9 is a flow diagram of a subroutine "DISPATCH" used to check the pedal value in the flow diagram of FIG. 8.

FIG. 9 illustrates in detail the subroutine DISPATCH. At the top of this program module, the pedal value, that is the value of the variable PEDAL is checked. In other words, a test is made to determine which pedal 61A, 61B or 61C is pressed, if any, by supplying an appropriate sequence of signals on line 168 (FIG. 7) so that the voltages at the inputs of multiplexer 154 are sequentially supplied to analog to digital converter 172 and appear in digital form on data line 176 for evaluation. A test is performed to determine whether or not the tooth number is to be updated. If a tooth update is requested, the current depth is frozen on the display 54. If tooth update is not to occur, the display is not frozen and the pedal registers "cleared" for the next time around through the foreground loop. After this initial test, the actual value of PEDAL is determined and an appropriate subroutine based on what that value is, is then performed. If PEDAL is zero, then no switch has been pressed, and subroutine NOEVENT is executed. If PEDAL equals one, the program flow is branched to a subroutine called ZEROSW (zero switch). If PEDAL equal two, flow branches to subroutine MEASSW (measure switch). If PEDAL equals three, the subroutine INCDEC (increment-decrement) is executed. This latter subroutine increments or decrements the tooth number.

If for any reason a spurious code appears in this subroutine for the variable PEDAL; that is, if one of the four allowable values is not found, the program flow falls through to recovery mode because the program is configured to recognize such a spurious code as the calling of a no-event function (NOEVENT). In any case, at the end of whatever subroutine is called, control is returned to the main foreground loop.

Figure 10A:
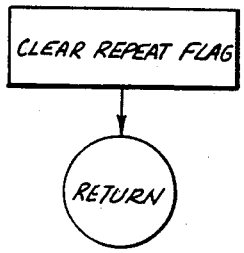
FIG. 10A is a detailed flow diagram of the subroutine "NOEVENT" of FIG. 9.

FIG. 10A is a detail of the subroutine NOEVENT. This subroutine simply clears the repeat flag. This flag is used to indicate whether the INCDEC routine for tooth number is being executed for the first time since the pedal was pressed or some subsequent iteration of the INCDEC subroutine is occurring.

Figure 10B:
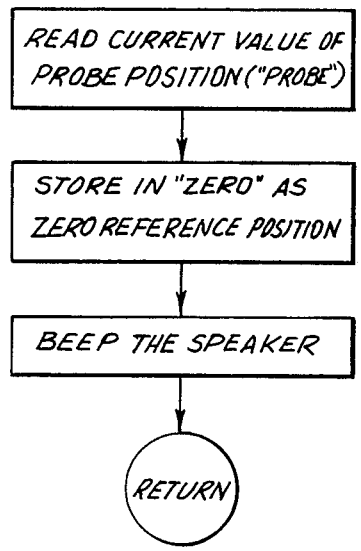
FIG. 10B is a detailed flow diagram of the subroutine "ZEROSW" of FIG. 9.

FIG. 10B illustrates the subroutine ZEROSW. In ZEROSW, first the current position of the probe member 78 with respect to probe tip 64 is read and the value is stored in a variable called ZERO. That is, the voltage produced by analog to digital converter 172 when the voltage supplied to its input is that on conductor 144C, is stored in variable ZERO. This zero reference value is subtracted from the current value representative of the position of probe member 78 with respect to probe tip 64 when it is desired to take a measurement. Thus, a signed number which indicates the displacement and the direction that the probe has been moved since switch 156A was last closed is obtained. At this time, a small feedback signal in the form of a beeping sound from a speaker (not shown) is also supplied. This allows the operator to know that the zero function has been executed without having to verify this by locking at display 54.

Figure 10C:
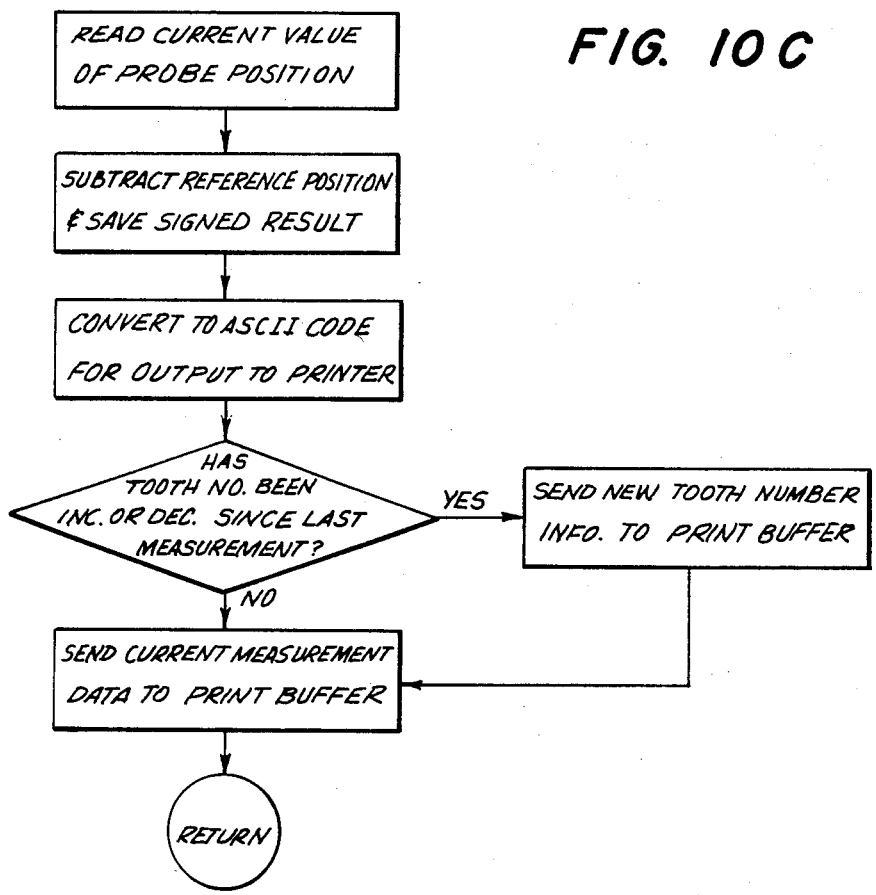
FIG. 10C is a detailed flow diagram of the subroutine "MEASSW" of FIG. 9.

FIG. 10C illustrates the subroutine MEASSW (measure switch). This subroutine reads the current analog value of probe position and subtracts from this number the value stored in the ZERO reference variable established by the ZEROSW routine of FIG. 10B. This produces a signed result which, as described above, indicates displacement and direction with respect to when the zero switch button was last pressed. This signed result is converted to millimeters units by a lookup table. An algorithm converts this millimeter number to ASCII code for output to printer 48.

The last part of subroutine MEASSW makes a check to see whether a measurement has been taken since the tooth number was last changed. If the measurement is the first since a tooth number update, the current tooth number is sent to the printer prior to information about this particular measurement. Control is then returned to recording the calling subroutine DISPATCH, discussed above.

Figure 10D:
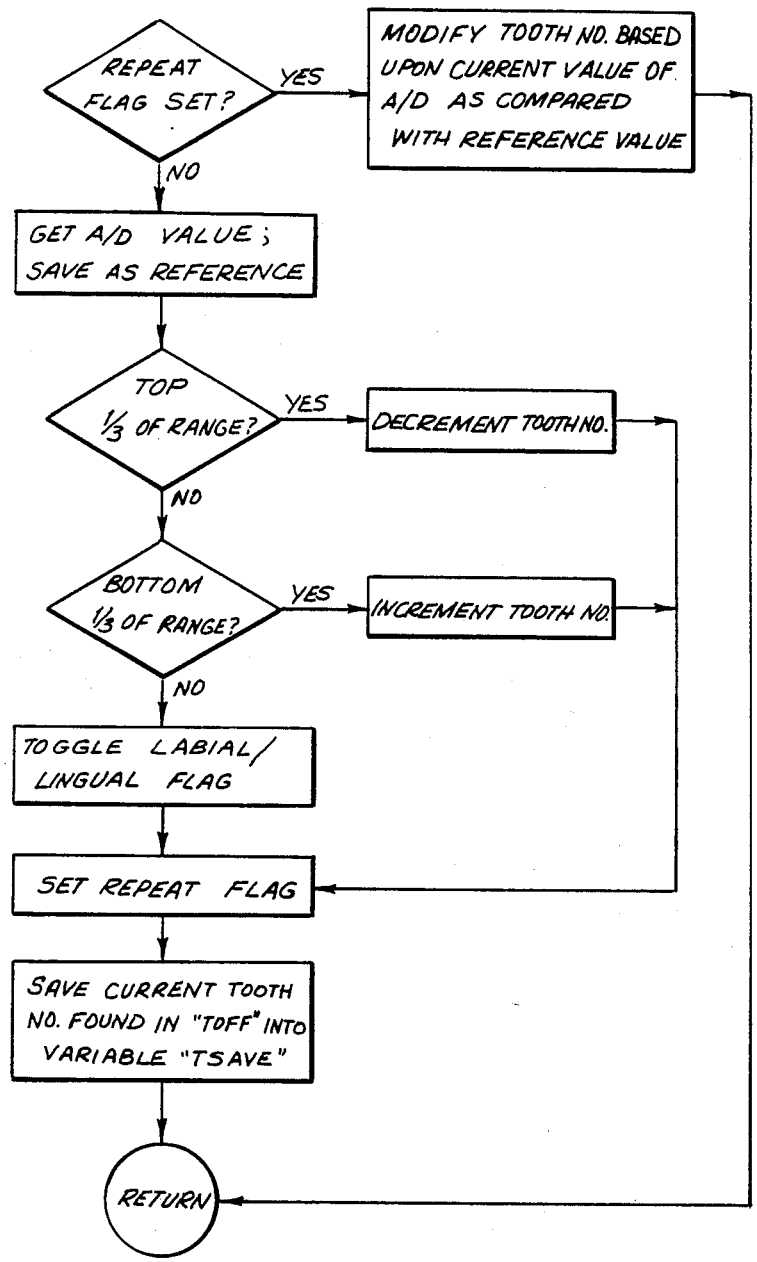
FIG. 10D is a detailed flow diagram of the subroutine "INCDEC" of FIG. 9.

FIG. 10D illustrates the subroutine INCDEC which is used during incrementing or decrementing of tooth number. If the tooth pedal (pedal 61C) is pressed, the DISPATCH subroutine will vector program flow to INCDEC. First a check is made to see if the repeat flag is set (FIG. 10A). This is a way of knowing whether this is the first time through this routine since the pedal was pressed or whether a subsequent iteration is being carried out, that is the pedal is still being held down since the last time INCDEC was executed. If the repeat flag is not set, which is the case when the pedal is first pressed, INCDEC supplies a signal on line 168 which causes multiplexer 154 to apply the voltage being produced by potentiometer 146 of probe 20 to the input to analog of digital converter 172. This number is then saved as a reference. A determination is then made as to whether or not this value is in the top third of the range.

If it is, due to the position of sleeve 108 along probe housing 68, the tooth number is decremented by one. If it is not, another check is made to determine whether the value is within the bottom one-third of the possible range of values due to the position of sleeve 108 along probe housing 168. If it is, the tooth number is incremented. If it is not, the probe is located in the middle third of the range and the value of the flag controlling whether labial or lingual gets printed after the tooth number, is toggled.

At this point, the repeat flag is set so that the software is provided with an input indicating that this subroutine has been executed once since the tooth number pedal was first pressed. During operation a current value for probe position has been saved as a reference. The operator has determined that the labial/lingual designation is correct. The value of the voltage produced by potentiometer 146 of probe 20 can be read on a continuous basis to increment or decrement the tooth number as required.

After the repeat flag is set, the current tooth number found in a variable called TOFF is saved by being moved into the variable TSAVE. The value of the tooth number in TOFF is the value currently being displayed on the screen. This is used in a fashion similar to the value of probe position stored above as a zero reference. That is, TSAVE is the tooth number from which positive and negative displacements are computed.

After executing the subroutine INCDEC for the first time, a return to DISPATCH occurs. DISPATCH then returns to the main loop of the program. The next time the program is executed, INCDEC is again executed from the start. On the following, and on subsequent executions, the repeat flag will be set. Instead of following the path marked NO and establishing references, the path marked YES will be followed. The tooth number will be modified as required based on current position of sleeve 108 as compared to the reference value. The difference is applied to the reference tooth number located in TSAVE. In other words, the signed difference between the current value associated with probe position and the reference is used to cause a similar change in the tooth number based on the reference value in TSAVE.

Figure 11:
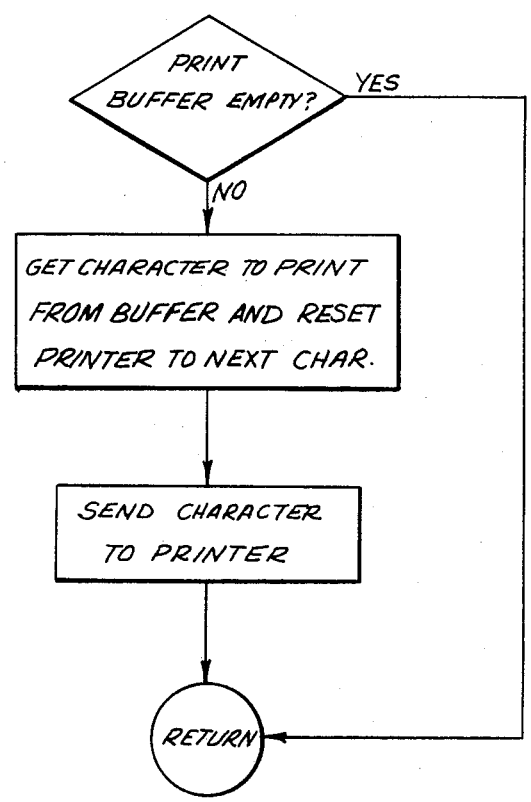
FIG. 11 is a detailed flow diagram of the subroutine "PRNTBUF" used in the main flow diagram of FIG. 8.

FIG. 11 is a detailed diagram of the subroutine PRNTBUF (print buffer). This routine services a RAM based buffer to temporarily store characters to be sent to the printer.

The function of PRNTBUF, as noted above, is to determine whether or not there is anything to print. If the buffer is empty, the program simply returns to the main routine. If there is something in the buffer to print, the first character thereof is sent to the printer. The pointer is then updated, and a return to the main program is made. One character is printed each time the foreground loop in the software is executed.

Printing in this manner provides time for microcomputer 32 to service other parts of various tasks associated with the operation of the apparatus such as updating the screen, reading the probe, and reading the foot switch. It thus appears that the microcomputer is doing all these things simultaneously. However, the printing of information by a printer is almost always peripheral bound; that is while the printer completes printing a character on paper, the CPU is capable of executing hundreds of instructions. Other tasks are completed during this available time.

Figure 12:
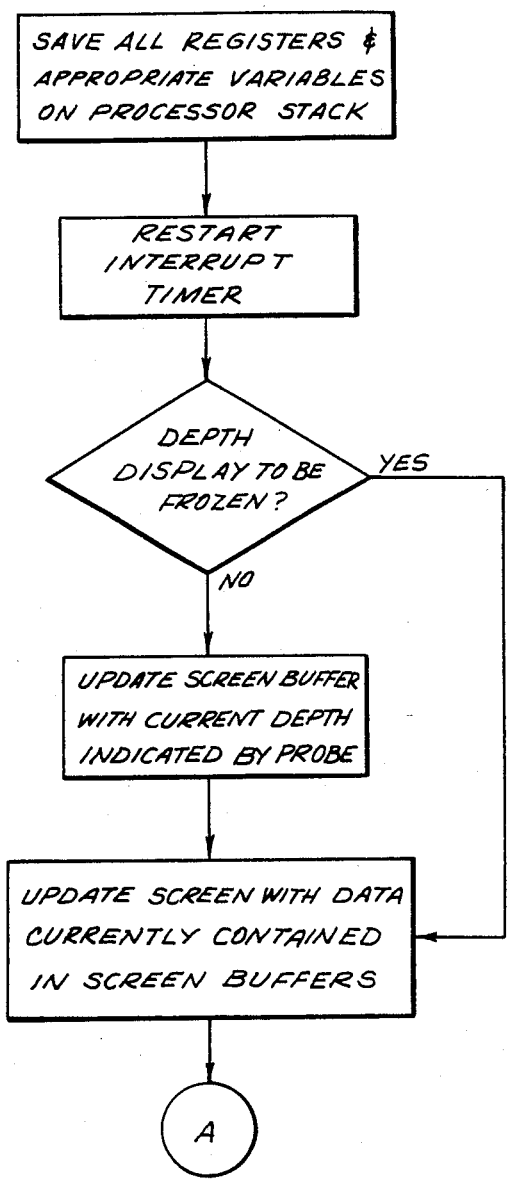
FIG. 12 is a detailed flow diagram of a first part of an interrupt routine "DEBOUNCE" used to interrupt the program of FIG. 8.

FIG. 12 is a detailed flow diagram of DEBOUNCE, an interrupt subroutine which is called by a timer function of microcomputer 32 to read the condition of the foot pedal switches and to validate data obtained therefrom. When an asynchronous event occurs it is generally designed as an interrupt which is a hardware initiated subroutine call, executed upon receiving a time-out from a counter.

When the transition from a program such as DISPATCH or MEASSW to DEBOUNCE occurs, it is necessary to save the values in all the registers and any variables which may be required in executing DEBOUNCE, on a processor stack, which is merely a specified portion of RAM memory. The interrupt timer is started again so that a constant time base continues. The period of the interrupt is approximately 40 milliseconds. Thus, DEBOUNCE is executed approximately 25 times every second.

After the timer has been reset, a check is made to determine whether or not the data displayed should remain the same, which is the condition which obtains if a tooth number change is being carried out. If tooth number is not being changed, line 168 is provided with a signal that causes the output of potentiometer 146 of probe 20 to be read. The current output value of the analog to digital converter is stored in a screen buffer for later display. If the tooth number is currently being changed, the program simply follows the path around this particular set of instructions, thus preventing both the tooth number and the depth indication from changing simultaneously on the screen. At this point the various buffers associated with the material written on the screen are assessed and the information is updated.

Figure 13:
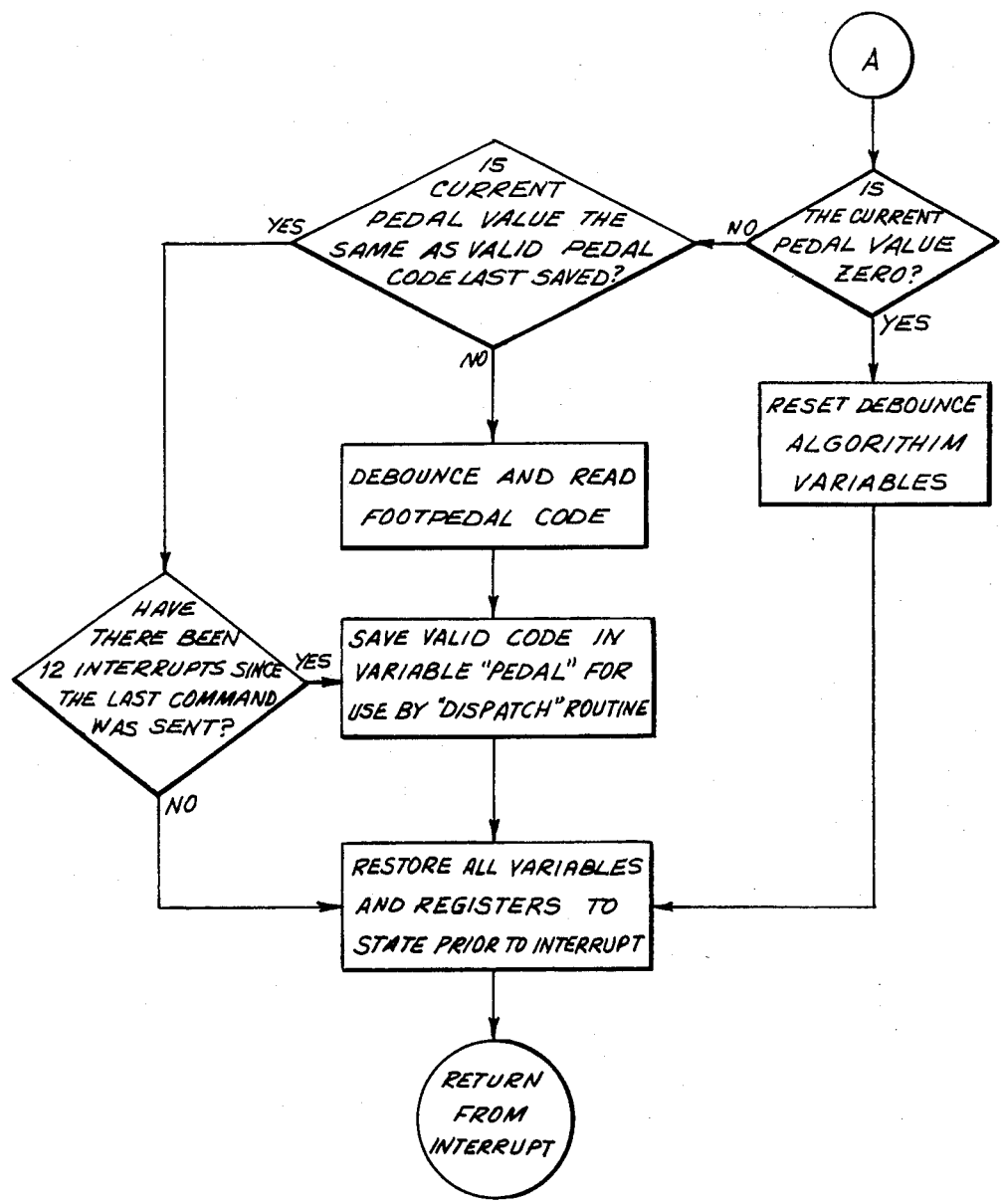
FIG. 13 is a second part of the subroutine "DEBOUNCE" of FIG. 12.

Referring to FIG. 13, when the point designated by the letter A in the subroutine of FIG. 12 is reached, the part of the subroutine which actually samples the condition of the foot pedal switch 60 on a periodic basis is executed. First, a check is made to see whether or not one of switches 156A, 156B or 156C is closed, at all. If no switch is closed, all the variables associated with the DEBOUNCE algorithm are reset and the procedure for restoring all the original variables and registers to their state prior to occurrence of the interrupt is carried out. Then, a transition is made into the foreground loop of the program at the point where the exit into the interrupt routine occurred.

If the check shows that the value for PEDAL is nonzero, that is, if one of switches 156A, 156B or 156C is pressed, the program then determines whether or not it is the same value that was found the last time this interrupt was executed (approximately 1/25 second before). If the value is the same, the dentist still has his foot on the pedal and desires to continue to execute a given foot pedal function.

Approximately 25 checks are run every second, which would cause the particular event the dentist is interested in to happen much too quickly. To slow down the response time, twelve or thirteen interrupts are counted before finally responding to the function being called. This creates the effect of repeating the desired function approximately every half second. After this half second delay, the code in the variable PEDAL (which is then used by the DISPATCH routine to direct the equipment to do whatever is required) is rewritten. An exit from the interrupt routine then takes place by restoring variables and returning to the main loop of the program.

Starting again from letter A in FIG. 13, a third condition is possible. First, the pedal value is found to be nonzero. Then the pedal value is found to be different from that which was found during the previous interrupt. This is the case, if for example, if PEDAL was zero (that is no switch had been pressed) and is then being pressed for the first time.

Since the pedal value is different, a series of program steps which essentially debounce the foot pedal switches to be certain that a valid value has been obtained, is executed. This series of steps reads the code coming from the pedal several times to verify that in fact the value of PEDAL has stabilized and that there is a real command present and not a spurious piece of information. If the value of PEDAL is determined to be an actual command, and not spurious information, the appropriate value is stored in the variable PEDAL again, for use by the subroutine DISPATCH and for controlling the instrument. After DEBOUNCE has been executed, program control returns to the main loop.

Figure 14:
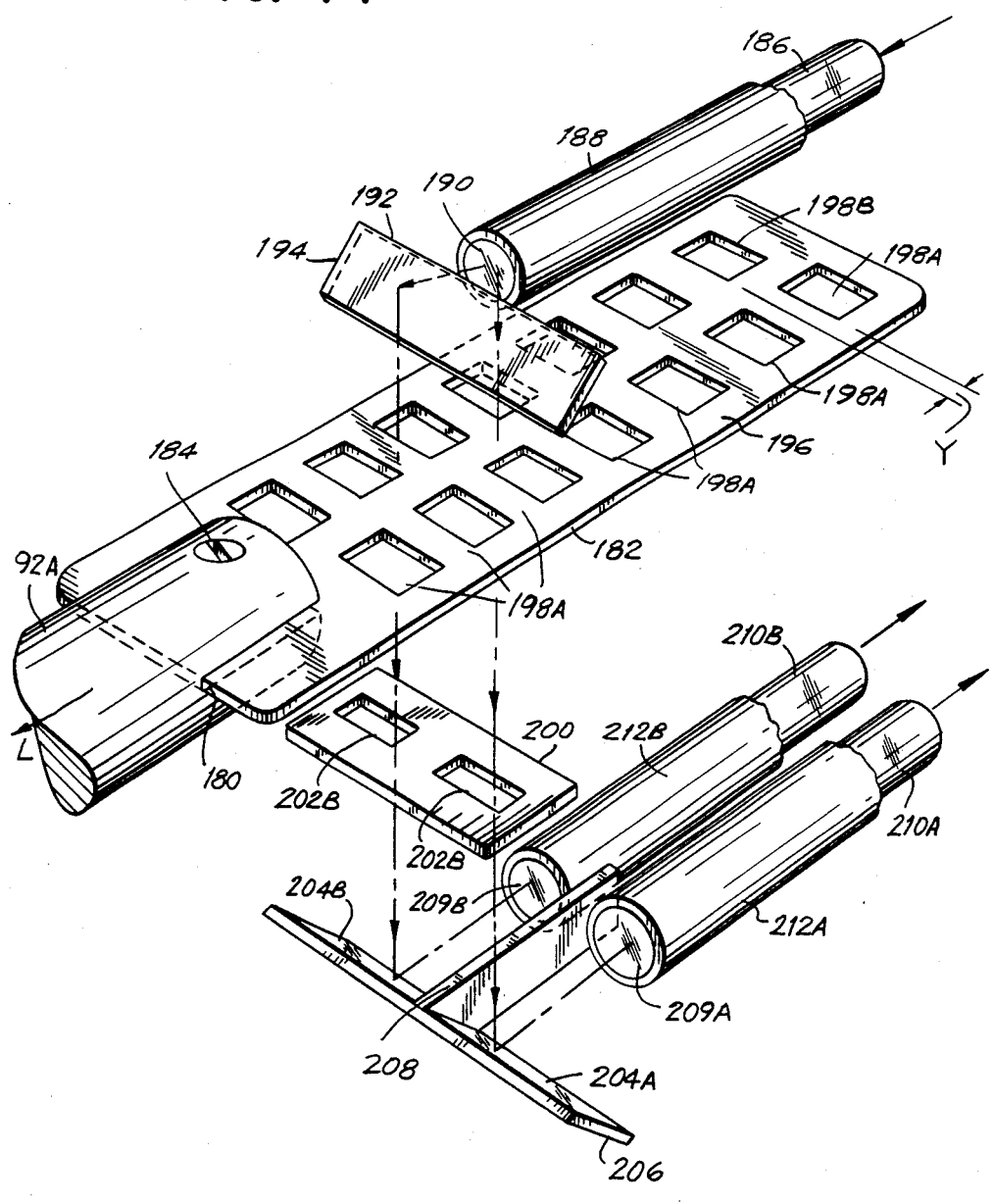
FIG. 14 is an exploded, perspective view of an embodiment of an encoder for the apparatus illustrated in FIG. 1.

FIG. 14 is an exploded perspective view directed to an encoder for use with an alternate embodiment of the probe illustrated in FIGS. 1 to 6. An actuating member 92A similar in structure and function to actuating member 92 is configured with a diametrically extending slot 180 instead of longitudinal slot 122 (FIG. 4). Slot 180 receives an opaque card 182 secured to actuating member 92A by a screw 184 extending through a radially extending hole from the outer surface of actuating member 92A to slot 180. A light conductor 186, of plastic fiber, for example, enclosed along its entire length by an opaque covering 188, conducts light from a light source to an end surface 190 of conductor 186. This light is reflected by a mirrored surface 192 of an upper reflection member 194. Light is reflected from surface 192 in a direction which causes it to travel perpendicularly to the major surface 196 of card 182. Card 182 is configured with a first series of openings 198A and a second series of openings 198B. Openings 198A are all of equal size and are spaced from one another by equal distances along the length of card 182. Openings 198B are of a size equal to that of openings 198A and are also spaced from one another by equal distances along the length of card 182. The spacing between openings 198A and 198B along the length of card 182 is identical. However, openings 198A are staggered with respect to openings 198B so that there is a distance Y between the borders of openings 198A and the borders of opening 198B extending in a direction perpendicular to the length of card 182. For example, openings 198A and 198B may each have a dimension in the direction of motion of card 182 of 0.50 mm. The spacing between openings 198A and 198B in said direction may then also be 0.50 mm. Distance Y is then preferably 0.25 mm. These dimensions will serve to provide a resolution of 0.25 mm in determining the extent of motion of card 182.

The relative positioning of the edges of openings 198A with respect to those of openings 198B provides a unique sequence of output light pulses for each direction of motion of card 182 in the direction of the longitudinal axis of actuating member 92A.

Light passing through openings 198A and 198B in card 182 then passes through a light baffle 200 having openings 202A and 202B, respectively. The light passing through openings 202A and 202B impinges upon reflective surfaces 204A and 204B of a lower reflecting member 206. An opaque separator 208 acts as a light baffle between two light conductors 210A and 210B each having respective opaque coverings 212A and 212B along their entire lengths. Light reflected from surfaces 204A and 204B, respectively, impinges upon end surfaces 209A and 209B of plastic fibre light conductors 210A and 210B, respectively, thus being conducted along said conductors. Conductors 186, 210A and 210B, surrounded by their respective opaque coverings, are formed into a fibre optic cable (not shown) similar to cable 26 for conveying data from probe 20 to circuit board 34 in housing 22. Housing 22 contains a light source (not shown) for supplying light to fibre optic light conductor 186 and suitable photodetection means for converting pulses of light received from conductors 210A and 210B into electrical signals. These components are of a type well known in the art such as a transmitter/receiver pair sold by Molex ® Corporation as Part No. 15-75-0002 and described in Application Note 15M entitled "Fiber Optic Links" published in October of 1985. Further, pulse conditioning circuits of a type also described in said Note, for converting the electrical signals into pulses useful as inputs for microcomputer 32 are located on circuit board 34.

FIGS. 15 and 16 illustrate a housing used to implement the illustrative embodiment of FIG. 14. Referring to FIG. 15, an upper housing member 212, shown in an inverted position is configured as a generally elongate member having a substantially semicircular cross section. An axially extending opening 214 is provided therein to receive light conductor 186. Light conductor 186 is positioned in opening 214 so that its end surface 190 projects into a V-notch 213 defined by sides 216 and 218 each at substantially a 45° angle with respect to the top planar surface 220 of member 212. Surface 218 is provided with a reflective coating so that light from conductor 186 will be reflected therefrom in a direction perpendicular to the longitudinal axis of member 212 and serves as mirrored surface 192 of FIG. 14.

Upper housing member 212 is configured with axially extending projections 222A, 222B, 222C and 222D which extend from the ends of member 212 towards V-notch 213 defined by walls 216 and 218. However, projections 222A, 222B, 222C and 222D terminate at a significant distance from V-notch 213.

Upper housing member 212 is designed to fit over lower housing member 224 of FIG. 16. Specifically, lower housing member 224 is configured with projections 226A, 226B, 226C and 226D. When so assembled, upper housing member 212 fits onto lower housing member 224 so that projections 226A and 226C are received between the inwardly facing ends of projections 222A and 222C. In a similar manner, projections 226B and 226D of lower housing member 224 are received between the inwardly facing ends of projections 222B and 222D of upper housing member 212. Thus, upper housing member 212 and lower housing member 224 when brought together form a substantially cylindrical body having a wide, longitudinal slot bounded by projections 222A to 222D and 226A to 226D. Card 182 is dimensioned so as to be received in said slot and so as to be capable of sliding axially along the length thereof.

Light from fibre optic conductor 186 reflected by surface 218 and passing through openings 198A and 198B of card 182 is reflected from a reflective surface 228 which together with another surface 230 define a V-notch 231 in lower housing 224. Surfaces 228 and 230 are disposed at an angle of substantially 45° with respect to planar surface 232 of lower housing member 224. An opaque separator 234 extends axially of lower housing member 224 and performs the function of separator 208 in FIG. 14. Light reflected from surface 228 travels to end surfaces 209A and 209B of fibre optic conductors 210A and 210B respectively.

The assembly of upper housing member 212 and lower housing member 224 is configured to fit within inner sleeve 69 of probe 20. Said assembly, together with card 182 serves as an optical encoder providing data on the extent and direction of motion of actuating member 92 and therefore probe member 78, thus allowing the dentist to take measurements of, for example, gingival pocket depth, penetration into the root canal, or the length of the clinical crown.

While the use of an optical encoder in probe 20 requires that some additional electronic components be used, analog to digital converter 172 and the analog multiplexer 154 of FIG. 7 can be eliminated. Further, the use of an optical encoder and fibre optic cables provides a significant advantage in that no electrical connections need be made to probe 20. Although, the voltage used to excite potentiometer 146 is quite low, it is still necessary to take precautions to assure patient safety. Further, whenever an electrical current is supplied to an apparatus coming into contact with a patient, rather stringent regulatory approval standards must be met. Thus, the use of a fibre optic data transmission path between probe 20 and housing 22 simplifies the regulatory approval process in as much as no electrical connection is made to the device coming into contact with the patient.

Figure 17:
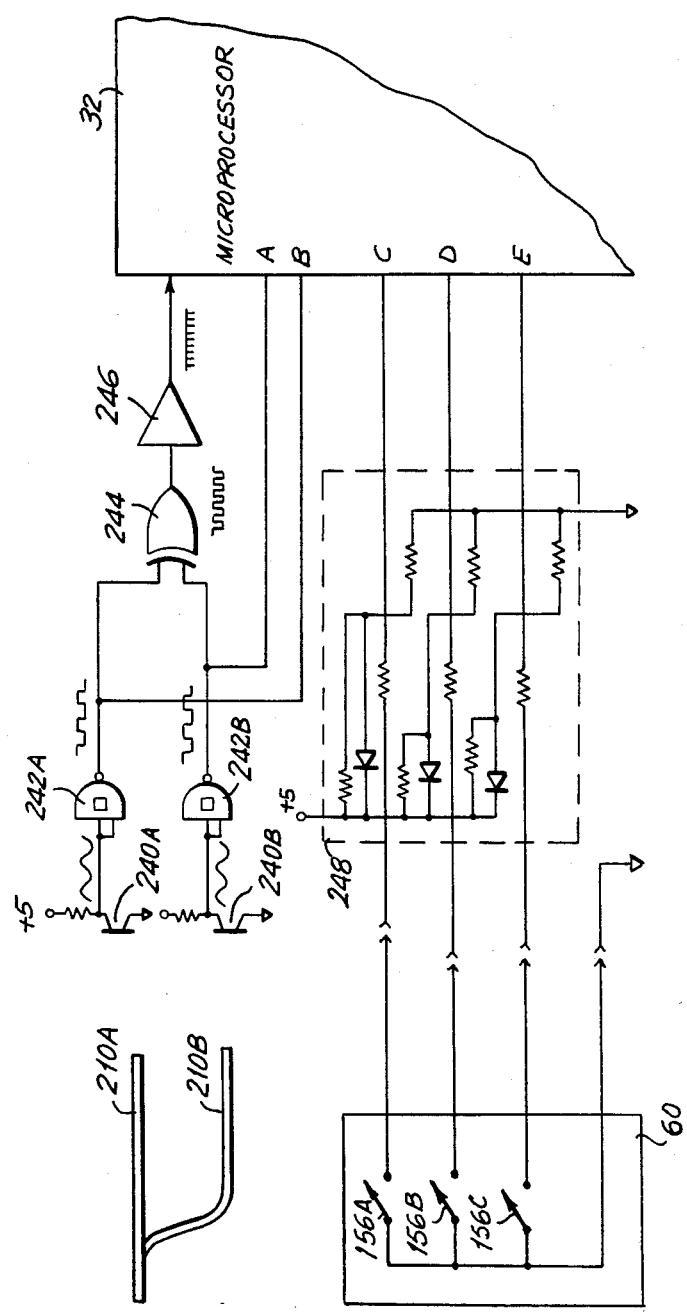
FIG. 17 is a schematic diagram showing the interconnection of components when the encoder of FIGS. 15 and 16 is used.

FIG. 17 illustrates a modified interface required for the optical encoder version of probe 20. Photodetectors 240A and 240B, which may be receivers of the Molex ® transmitter/receiver pair mentioned above respond to light signals from fiber optic conductors 210A and 210B, respectively in a pseudo-digital fashion. Schmitt trigger logic gates 242A and 242B are used to condition the photodetector outputs of photodetectors 240A and 240B respectively into usable digital square waves. The two resulting pulse trains are fed into an EXCLUSIVE-OR gate 244. The output of gate 244 is connected to an edge detector circuit 246 which in turn produces a pulsed output each time a transition is detected at the input thereof.

When encoder card 182 slides within the encoder housing, the light from fibre optic conductor 186 is interrupted and light pulses are received at photodetectors 240A and 240B which are mounted on circuit board 34. The spacing and positioning of the two sets of holes on card 182 are such that a transition detected on either channel indicates displacement of 0.25 mm and the specific states immediately before and after the transition indicate positive or negative direction of travel.

Edge detector circuit 246 produces a pulse each time there is a transition on either of the channels provided as an input to gate 244. The pulse output af edge detector 246 is fed into a non-maskable interrupt input of microprocessor 32 to cause it to immediately add to or subtract 0.25 mm from the current position of the probe member.

The interrupt subroutine is used to determine whether the displacement that occurred was positive or negative by reading the status of the outputs of Schmitt trigger gates 242A and 242B through two input bits A and B of a digital input port of microcomputer 32. The program compares the current state of the two bits with the previous state of the bits and either adds or subtracts 0.25 mm to the current measurement value, as appropriate and as more fully described below.

The switch data from foot pedal switch 60 is routed through a static protection circuit 248, similar to the one described with respect to FIG. 7, and then connected directly to three other input bits C, D, and E of a digital input port of microcomputer 32. It is not necessary to use an A/D converter to read the open and closed status of a single throw toggle switch, such as switches 156A, 156B and 156C of foot pedal switch 60 because the outputs are inherently digital and require no A/D conditioning.

When using the encoder according to FIGS. 14 to 16, in order to modify tooth number, it is necessary to move sleeve 108 after switch 61C is pressed, as there is no absolute reference of the position of card 182.

FIG. 18A represents, in chart form, the data produced by Schmitt trigger logic gates 242A and 242B. Channel A is representative of the light pulses associated with conductor 210A while channel B is representative of pulses associated with conductor 210B. Further, table 1 is representative of data produced when card 182 moves to the right, while table 2 is representative of data produced when card 182 moves to the left. The sequence of pulses produced is a direct result of the staggered placement of openings 198A and 198B, as discussed above. It will be noted that the sequence of data produced when card 182 moves to the left is the reverse of the sequence produced when card 182 moves to the right.

Figure 19:
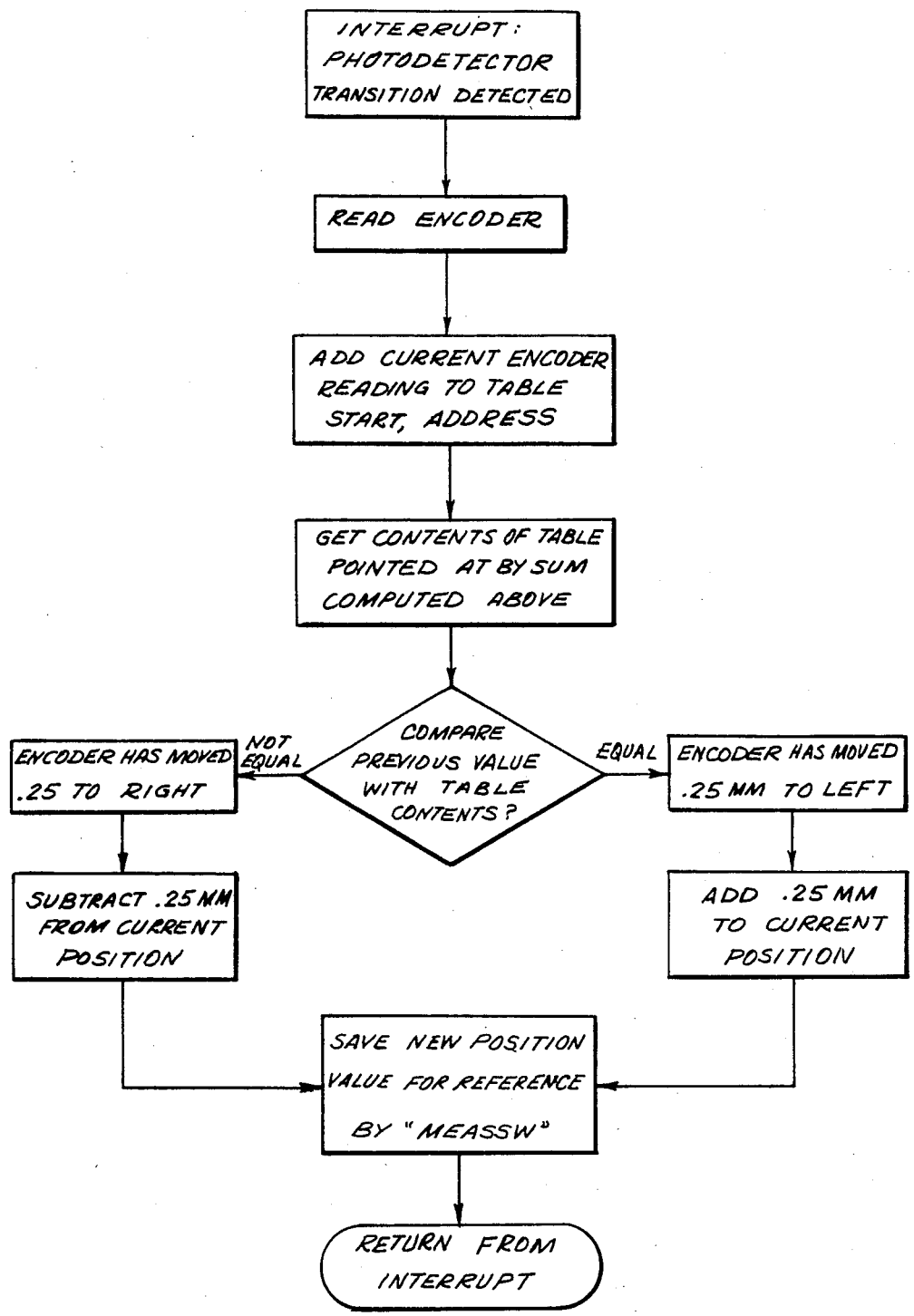
FIG. 19 is a detailed flow diagram illustrating computation of the direction and extent of motion in response to the data of FIG. 18.

FIG. 18B illustrates, in table 3, a lookup table which may be used in conjunction with the software algorithm flowcharted in FIG. 19. FIG. 19 is a detailed representation of the steps necessary for computing the direction and extend of motion of probe member 78 when the encoder of FIGS. 14 to 16 is used. As such, the steps illustrated in FIG. 19 produce a value which is provided to the first functional block of the subroutine MEASSW of FIG. 10C since analog to digital conversion is not required.

The program flowcharted in FIG. 19 is executed each time the edge detector circuit 246 detects a transition on one of the photodetector inputs. First, the digital data at input ports A and B are read and formatted as a binary number between zero and three. This number is added to the beginning address of a four byte lookup table containing data indicating travel in the left direction. If the data contained in the memory location pointed to by this sum is equal to the previous data, i.e., the data read at the last transition, then the direction of travel was to the left. If the table contents and the previous data are not equal, then travel was to the right. The program then adds to or subtracts 0.25 mm from the current probe position, as appropriate. This current probe position number is equivalent to the probe position value available from the A/D converter of FIG. 7.

It is possible to make various modifications to the invention. For example, to facilitate the use of location routines other than those specified herein, such as a complete lingual examination followed by a complete labial examination, a series of switches (not shown) may be provided at the back of housing 22. These switches, providing inputs to microcomputer 32 at selected times controlled by the software configuration, may be used to change the predetermined location sequence, thus adding flexibility for diagnostic routines following different standards. Further, means may be provided for entering or storing previous data so that printer 48 provides an output indicating both current and previous measurements of, for example, gingival pocket depth. Such a data configuration is useful for following the progress or recession of periodontal disease.

The apparatus of the present invention may also be used to assist in determining the depth of packing of a root canal. Probe member 78 may be moved with respect to end 72 of probe tip 64 under the action of control sleeve 108 to assist in placing material into the root canal. When the apparatus of the invention is used in this manner, an indication of the depth to which the material has penetrated along the root canal is provided.

In this context, it will be understood that the location specified for a measurement need not be a tooth number. Some of the teeth have multiple roots and the location specified is then a designation of the root being probed.

It will also be understood that the apparatus of the present invention may be used to measure the gap between teeth due to occlusion by proper positioning of end 72 of tip 64. It is recognized that such distances are generally smaller then those measured when evaluating gingival pockets or depths of penetration into a root canal. As such, adequate provision must be made to assure sufficient resolution for the measurements required.

It is also possible for the printer to be located so as to not be an integral part of the housing 55. A standard 8½ inch wide printer, such as the Epson MX-80 may be used in conjunction with the periodontal data collection apparatus of the present invention.

To enhance the presentation, acceptance of the technique and general feeling of familiarity with the generated report, preprinted periodontal tractor-fed forms may be utilized. The probe software would then acquire and store examination data, and upon command, print the numeric values of pocket depth in the appropriate locations on the standard form and graphically annotate the tooth illustrations as is commonly done by hand. Different forms or even blank paper in certain cases combined with the appropriate output formatting routines would enable the device to perform a broad array of functions.

The function of comparisons of data from a current examination to that of a previous examination, may be performed in a general purpose microcomputer environment. A serial communication port for connection of data output lines on circuit board 34 to almost any personal computer may be provided. A patient's periodontal history may be maintained on a floppy disk by downloading current examination data from the apparatus of the present invention to a personal computer. A variety of readily available statistical and graphical software may then be used to effect the most meaningful representation of the progress or recession of a patient's periodontal disease. A number of front panel pushbuttons (not shown) may be provided on housing 55 to control system functions such as printing, downloading, uploading, measurement units, scaling, special report annotations, etc. A special attachment tip may be provided to allow bite spacing measurements.

Printed reports may be generated by outputting formatted data to a standard off-the-shelf printer. To minimize printing time and to enhance the appearance of the report, preprinted forms may be utilized. The data may be written or graphed onto the appropriate locations on the form.

As noted above a personal computer periodontal history database may be used for monitoring patient response to treatment. This may be in the form of menu-driven application software for accepting examination data from the apparatus of the present invention and for entering the data in the record of the particular patient. Several statistical and graphical reporting formats may be utilized to present the acquired data. In addition, recommendations for specific generally accepted treatments based upon periodontal examination data may be offered to the dentist.

It is desirable for the apparatus of the present invention to be as flexible as possible to permit application to new procedures as they are identified or developed. The reference above to "uploading" contemplates a capability of the apparatus of accepting instructions from the personal computer which would modify some aspect of normal operation or provide a new functionality. The primary use contemplated for this feature is to change the format of printed report data to address some special application requirement.

It is also envisioned that control sleeve 108 may be eliminated entirely by providing a mechanical actuator (not shown) for probe member 78. Such actuator may be positioned within probe housing 68 but if electrically activated would defeat the advantages noted above for an optical encoder. An alternative approach is to mount such actuator on circuit board 34 and connect it to actuating member 92 with a flexible but substantially nonextensible elongate member such as a steel wire.

It will thus be seen that the objects set forth above, among those made apparent from the preceding description, are efficiently attained and, since certain changes may be made in the above construction without departing from the spirit and scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. An apparatus for measuring distance between points in the mouth of a patient undergoing medical or dental diagnosis or treatment, said apparatus comprising:
    a housing having an end thereof placeable adjacent to a first of said points;
    a distance measurement means coupled to said housing, said distance measurement means producing at least one output signal representative of the distance between two points in the mouth;
    an analyzing means responsive to said output signal for reporting the measured distance; and
    means for selectively specifying a location in the mouth corresponding to a measurement being made.

2. The apparatus of claim 1, further comprising generating means for generating a permanent record of each location specified and of each measured distance proximate said location.

3. The apparatus of claim 1, further comprising display means for displaying numbers representative of each measured distance and each specified location corresponding to said measured distance.

4. The apparatus of claim 1, further comprising display means for displaying a number representative of said measured distance.

5. The apparatus of claim 1, wherein said analyzing means comprises a microcomputer.

6. The apparatus of claim 1, wherein said distance measurement means comprises a member coupled to and movable with respect to said housing, an end of said member being movable from the first of said points to a second of said points while said housing is held in a fixed position with respect to said points, said distance measurement means producing said output signal so as to be representative of extent of movement of said member.

7. The apparatus of claim 6, wherein said distance measurement means further comprises a potentiometer having a portion thereof coupled to said member, said potentiometer being for generating said signal, and said signals being an analog voltages.

8. The apparatus of claim 6, wherein said distance measurement means further comprises an optical encoder having a portion thereof coupled to said member, said optical encoder being for generating said signal, and said signals being pulses of light.

9. The apparatus of claim 1, and further comprising:
    means responsive to a command for causing said analyzing means to interpret said output signal as zero when said member is at a predetermined position with respect to said housing.

10. The apparatus of claim 1, wherein the analyzing means processes data in a number of modes and is responsive to at least one mode selection signal for selecting a mode of operation, and further comprising:
    input means for providing a mode selection signal to said analyzing means for determining the mode of operation of said analyzing means.

11. The apparatus of claim 10, wherein said input means comprises a foot pedal which is movable to provide at least one mode selection signal to said analyzing means.

12. The apparatus of claim 11, wherein said analyzing means includes a microcomputer and a program storage means for storing a program for said microcomputer.

13. An apparatus for measuring the distance between points in the mouth of a patient undergoing dental diagnosis or treatment, said apparatus comprising:
    a housing having an end thereof placeable in the mouth;
    an elongate probe means slidably mounted in said housing so that an end thereof is movable from a first point to a second point when the end of said housing is placed at one of said first and second points;
    a probe actuating means for causing said probe means to slide in said housing;
    a motion inhibiting means coupled between the housing and the probe means for preventing movement of the probe means until a predetermined level of force is applied thereto;
    a motion detection means responsive to motion of said probe with respect to said housing, said motion detection means providing an output useful for determining the position of said probe with respect to said housing; and
    an analyzing means responsive to said output for reporting said distance.

14. The apparatus of claim 13, wherein said probe actuating means is manually activated.

15. The apparatus of claim 13, wherein said probe actuating means comprises:
- a first member disposed in said housing and slidable therein, said probe being coupled to said first member;
- a second member disposed outside said housing;
- a connecting means for rigidly coupling said first member to said second member so that motion of said second member with respect to said housing causes said first member and said probe means to move with respect to said housing.

16. The apparatus of claim 15, wherein said housing has an opening for said connecting means.

17. The apparatus of claim 15, wherein said opening in said housing is a slot extending longitudinally of said housing.

18. The apparatus of claim 16, wherein said second member comprises a sleeve extending about a circumference of said housing and wherein said sleeve has a central portion of smaller diameter than either end thereof.

19. The apparatus of claim 13 wherein said housing has an end portion which is detachable from said housing, said probe means being slidable in said end portion.

20. The apparatus of claim 13, wherein said probe means is detachable from said probe actuating means.

21. The apparatus of claim 13, wherein said housing has an end portion which is detachable from said housing, said probe means is slidable in said end portion, and said probe means is detachable from said probe actuating means, said end portion of said housing and said probe means being replaceable units of said apparatus.

22. The apparatus of claim 13, wherein said probe means is a nonmetallic member.

23. The apparatus of claim 13, wherein said probe means is comprised of a nylon or polyvinyldifluoride monofilament.

24. The apparatus of claim 13, wherein said probe means is radio-opaque.

25. The apparatus of claim 13, wherein said motion detection means comprises a potentiometer and electrical energy means for providing electricity to excite said potentiometer.

26. The apparatus of claim 13, wherein said motion detection means comprises an optical encoder means and light supply means for providing light to said optical encoder means.

27. The apparatus of claim 26, wherein said optical encoder means includes a movable member, said movable member being coupled to said probe means so that motion of said probe means occurs with corresponding motion of said member, said member having a first pattern for interrupting transmission of light by said member, said member also having a second pattern for interrupting transmission of light by said member, the occurrence of interruption of light by said first pattern and by said second pattern being said output.

28. The apparatus of claim 27, wherein said patterns are configured so that the number of occurrences of interruption of light by at least one of said first pattern and second pattern indicates the magnitude of displacement of said probe means.

29. The apparatus of claim 27, wherein said patterns are configured on said member so that relative occurrence of interruption of light by said first pattern and by said second pattern is indicative of direction of motion of said probe means.

30. The apparatus of claim 27, wherein said first pattern and said second pattern are of substantially identical configuration, said first pattern being displaced from said second pattern in the direction of motion of said movable member by a predetermined distance.

31. The apparatus of claim 27, wherein said optical encoder means further comprises a first light conductor for supplying light to illuminate a portion of each said patterns, second and third light conductors for receiving light from said first and second patterns, respectively, and photodetector means at respective ends of said second and third light conductors removed from said member.

32. The apparatus of claim 31, wherein said first, second and third light conductors form a fiber optic cable, said light supply means and said photodetector means being located at a distal end of said cable with respect to said optical encoder means.

33. The apparatus of claim 13, wherein said analyzing means comprises:
- interpreting means for providing an interpretation of said output; and
- display means for displaying said interpretation.

34. The apparatus of claim 13, wherein said motion inhibiting means comprises a member extending from said actuating means into contact with a surface associated with said housing, and means for adjusting the level of frictional engagement of said member with said surface to set the level of force required to move said member relative to said surface.

35. The apparatus of claim 34, wherein said member is an annular ring, and said surface is an internal surface of said housing.

36. The apparatus of claim 35, wherein said adjustment means comprises a screw fitted in a cylindrical opening in said actuating means, and wherein the relative position of said screw with respect to said annular ring determines magnitude of said frictional forces.

37. An apparatus for providing a record of data including distance measurements and location identifying data associated with said distance measurements, said apparatus comprising:
- designating means for selectively providing identifying data corresponding to at least one location;
- acquisition means for acquiring measurement data related to at least one distance associated with the identified location;
- means for converting the measurement data to distance measurement data; and
- data processing means for assembling said identifying data and said distance measurement data to form said record.

38. The apparatus of claim 37, wherein said location identifying data corresponds to a location in the mouth of a patient undergoing dental diagnosis or treatment and wherein said distance measurement data corresponds to the distance between selected points in said mouth.

39. The apparatus of claim 37, and further comprising:
- control means coupled to the designating means for selectively causing said designating means to change said identifying data to correspond to a second location.

40. The apparatus of claim 39, wherein said location identifying data comprises a series of numbers each of which corresponds to a location and said control means selectively causes one of said numbers to be increased or decreased.

41. The apparatus of claim 37, further comprising display means for displaying said first data and said second data as said second data is acquired.

42. The apparatus of claim 40 wherein said control means successively increases or decreases said number to attain a number which identifies a selected location.

43. The apparatus of claim 39 wherein said acquisition means comprises a probe which provides at least one measurement data signal.

44. The apparatus of claim 43 wherein said probe provides first and second measurement data signals which define a measured distance.

45. The apparatus of claim 43 wherein said probe further comprises:
 a member which is movable between first and second positions; and
 potentiometer means for providing a measurement data voltage output signal whose level varies as a function of the distance between said two positions.

46. The apparatus of claim 43 wherein said probe further comprises:
 a member which is extendable from said probe, said member being movable relative to said probe through a distance to be measured; and
 pulse generating means coupled to said member for providing a measurement data signal.

47. The apparatus of claim 46 wherein said pulse generating means comprises an optical encoder which is coupled to said member and further comprising:
 optical fiber means for supplying light to said optical encoder and for conveying light pulses therefrom as the measurement data signal for said data processing means.

48. The apparatus of claim 40 wherein said location designating means responds to a control signal to determine whether said number is to be increased or decreased, and further comprising:
 probe means comprising a probe member, a housing, a probe which is movable relative to the housing, and a signal generator responsive to one of a position of the probe and movement of the probe relative to the housing to provide said control signal.

49. The apparatus of claim 43 wherein said location designating means responds to a first control signal to select the direction of change of said number and to the duration of a second control signal to determine the number of steps by which said number is changed.

50. The apparatus of claim 49 wherein said designating means responds to a third control signal to change the identity of the sequence of locations.

51. The apparatus of claim 49 wherein said first control signal is a measurement data signal from said probe.

52. The apparatus of claim 49, and further comprising:
 pedal means for generating said second control signal.

53. The apparatus of claim 37 wherein the data processing means responds to a control signal to store said location identifying data and said distance measurement data, and further comprising:
 switch means for generating the control signal.

54. The apparatus of claim 53 wherein said switch means is foot actuated.

* * * * *